US008343505B2

(12) United States Patent
Kuo et al.

(10) Patent No.: US 8,343,505 B2
(45) Date of Patent: Jan. 1, 2013

(54) SUBUNIT VACCINE FOR AQUACULTURE

(75) Inventors: Tsunyung Kuo, I-Lan (TW); Gabriel Hsuchung Chen, Taipei (TW); Chungchin Wu, I-Lan (TW); Oystein Evensen, Oslo (NO); Inderjit Singh Marjara, Oslo (NO)

(73) Assignee: Schweitzer Co., Ltd., Taipei (TW)

( * ) Notice: Subject to any disclaimer, the term of this patent is extended or adjusted under 35 U.S.C. 154(b) by 202 days.

(21) Appl. No.: 12/746,409

(22) PCT Filed: Dec. 4, 2007

(86) PCT No.: PCT/CN2007/003438
§ 371 (c)(1), (2), (4) Date: Aug. 27, 2010

(87) PCT Pub. No.: WO2009/070929
PCT Pub. Date: Jun. 11, 2009

(65) Prior Publication Data

US 2010/0316663 A1 Dec. 16, 2010

(51) Int. Cl.
*A61K 39/12* (2006.01)
*A61K 39/295* (2006.01)

(52) U.S. Cl. ................ 424/192.1; 424/204.1; 424/236.1

(58) Field of Classification Search ........................ None
See application file for complete search history.

(56) References Cited

U.S. PATENT DOCUMENTS 7,807,144 B2 * 10/2010 Yang et al. .................. 424/93.2

FOREIGN PATENT DOCUMENTS

WO WO2009070929 6/2009

OTHER PUBLICATIONS

Riley et al (Aquaculture 112:271-282, 1993).*
Crane et al (Viruses 3:2025-2046, 2011, not prior art).*
Munang'andu HM, et al. ("Comparison of vaccine efficacy for different antigen delivery systems for infectious pancreatic necrosis virus vaccines in Atlantic salmon (*Salmo salar* L.) in a cohabitation challenge model." Vaccine (2012), http://dx.doi.org/10.1016/j.vaccine.2012.04.039) (10 pages; in press, available online Apr. 23, 2012, not prior art).*
PCT International Search Report dated Sep. 25, 2008 for PCT/CN2007/003438.
PCT Written Opinion of the International Searching Authority dated Sep. 25, 2008 for PCT/CN2007/003438.
PCT International Preliminary Examination Report dated Mar. 4, 2010 for PCT/CN2007/003438.
PCT Notice Informing the Applicant of the Communication of the International Application dated Jul. 9, 2009 for PCT/CN2007/003438.
PCT Information Concerning Elected Offices Notified of Their Election dated Jun. 11, 2009 for PCT/CN2007/003438.

* cited by examiner

*Primary Examiner* — Mary E Mosher
(74) *Attorney, Agent, or Firm* — WPAT, P.C.; Anthony King

(57) ABSTRACT

An aquatic subunit vaccine comprises an antigenic fusion protein and suitable carrier or adjuvant. The antigenic fusion protein sequence consists from its amino terminus to carboxyl terminus of a receptor binding motif and a translocation domain of *Pseudomonas aeruginosa* exotoxin A and has the amino acid sequence of SEQ ID No: 8; a viral antigenic protein affecting fish disease; and a signal peptide having the amino acid sequence of SEQ ID No: 10.

9 Claims, 4 Drawing Sheets

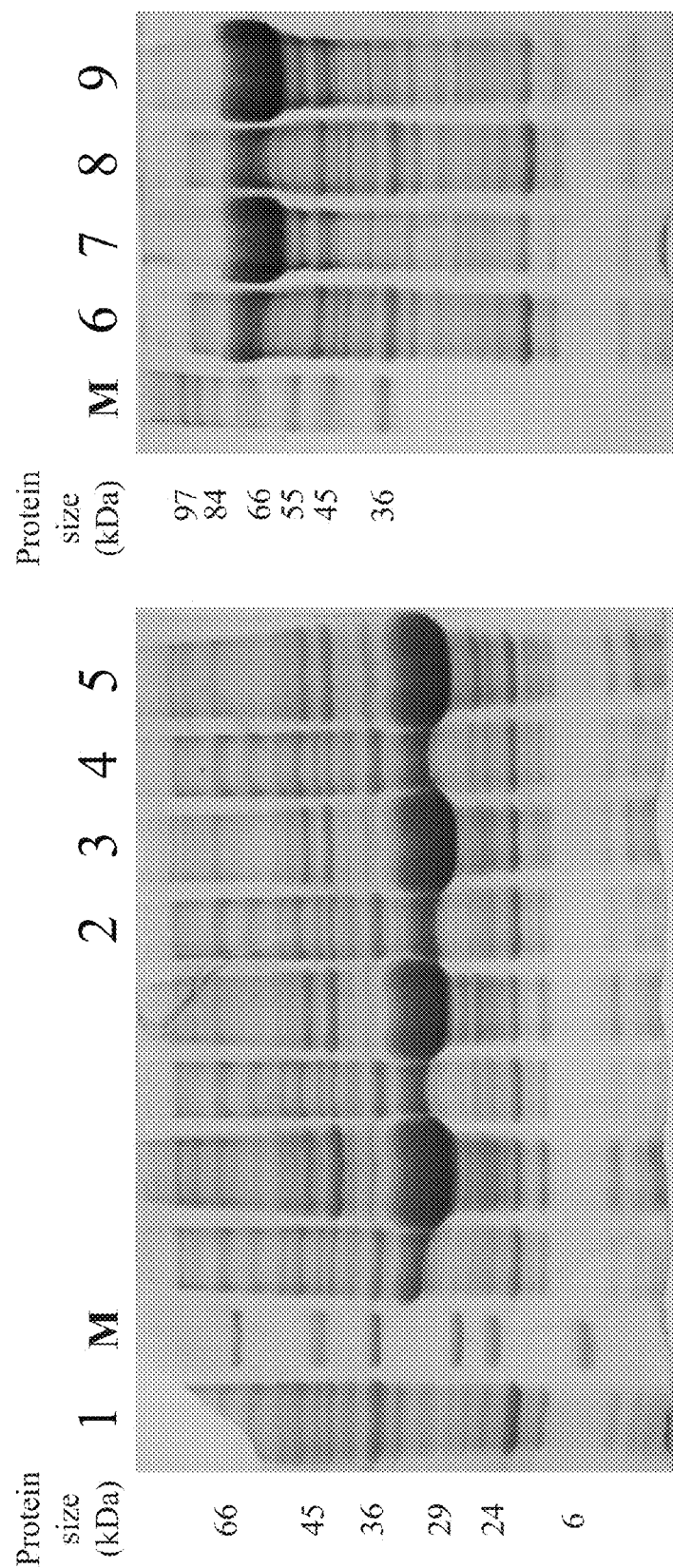

SUBUNIT VACCINE FOR AQUACULTURE

BACKGROUND OF THE INVENTION

1. Field of the Invention

Figure 1A:
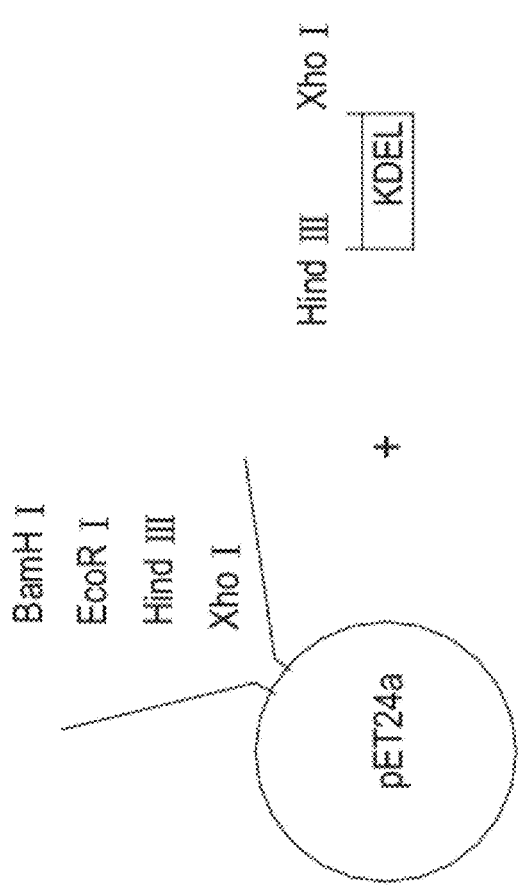

The invent relates to aquatic subunit vaccine and in particular, to an aquatic subunit vaccine prepared based upon recombinant DNA technology by fusing a fish antigenic protein with the receptor binding motif and the translocation domain of an exotoxin A, as well as with the signal peptide of KDEL.

2. Description of the Prior Art

Infectious Pancreatic Necrosis (IPN) is a worldwide highly contagious fish disease. Infectious Pancreatic Necrosis Virus (IPNV), the pathogen of IPN, belongs to the family of Birnaviridae. The genome of IPNV consists of two segments of double-stranded RNA (dsRNA), segments A and B. The virion is a non-enveloped icosahedron particle. The length of the A segment gene is 3.2 Kb and codes predominantly for primary virus binding protein (VP2), secondary virus binding protein (VP3), and enzyme protein (VP4).

The major hosts of Infectious Pancreatic Necrosis Virus are salmon and trout. Other economical fishes and shells like eels, barracudas, cods, tilapias, pond loaches, milkfish, and clams, had been found to be infected by IPNV. IPNV affects primarily the young fish of salmon and trout in the initial feeding stage. The young fish in the weeks of initial feeding stage and later in the freshwater stage are vulnerable to IPNV infection. Nevertheless, in the mid 1980's, indications of IPNV disease outbreaks in post-smolt salmons held in seawater had also been reported. IPNV can be traced in the primary Atlantic salmon aquaculture countries such as Chile, America, and Norway. In Norway, IPN is one of the most serious contagious fish diseases in the salmon aquaculture industry. IPNV can cause a mortality of near 100% in freshwater stage of salmon. In post-smolt salmons, the mortality of IPNV may range from 10-20% up to 70%. Therefore, IPNV is a severe threat, ecologically and economically, to the aquaculture and sea-farming industries.

Vaccination against IPNV is the major control approach used in the salmon aquaculture industry. Conventional aquatic vaccines against IPNV includes mainly two types, the pathogen killed vaccine and the subunit vaccine. The development of pathogen-killed vaccine requires cell lines non-infected by other viruses. However, the fish cell lines are uncommon and the options are rare in addition to its difficulty in development as well as the high cost therefore. Subunit vaccine can be manipulated by genetic engineering technology. VP2 protein of IPNV expressed by *E. coli* or structure proteins of IPNV expressed by Insect Baculovirus are two common types of IPNV subunit vaccines that can induce the specific antibody responses in salmons. However, protective immunological effects offered by those approaches described above can not satisfy the standard required in the aquaculture industry.

There are several theories as to why a subunit vaccine against viruses can not induce a protective immunity. Concepts that have several proponents are as follow:
1) the antigen can not properly targeted to the cell that plays the key role in inducing immunity;
2) the antigen may be trapped in exogenous routes and not transported into cytoplasm of a target cell to associate with its endoplasmic reticulum; and
3) as a consequence of the foregoing, the antigen may not be presented to the effector cell in the correct context.

Accordingly, there are a lot of drawbacks associated with conventional aquatic vaccines and improvements thereof have to be improved urgently.

In recent years, as rapid development of biotechnologies, genetic engineering approaches are utilized to modify and alter genes, thereby microorganisms originally harmful to human being or animals can be transformed into beneficial tools in medical and agricultural application. For example, *Pseudomonas aeruginosa* is one of typical examples among these organisms. When a patient with cystic fibrosis is infected by *Pseudomonas aeruginosa* may develop often chronic respiratory tract infection followed with chronic pneumonia. As cancer patients with immunodeficiency or patients severely burned are infected by *Pseudomonas aeruginosa* tend to turn into acute pneumonia or sepsis. The main factor in causing diseases to infected patients is the exotoxin A produced by *Pseudomonas aeruginosa*.

The protein structure of exotoxin A consists of three major functional domains. Domain I of exotoxin A is a receptor-binding domain that is responsible for binding with $\alpha$2-macroglobulin/LDL receptor on the plasma membrane of a mammalian cell to form an internalized ligand-receptor complex and then enters into the endosome of the cell through endocytosis. Where it will be localized and processed by proteases within the endosome. After enzymatic cleavage of exotoxin A in endosome, truncated protein fragments containing domain II (the translocation domain) and the toxic domain III are released and further translocated under the action of the translocation domain II from endosome into cytoplasm where it will bind with Golgi body and endoplasmic reticulum (ER) to form reticulum-Golgi network. Then, the third domain of truncated exotoxin A enables to inhibit protein synthesis in the cell, resulting in cell death.

Currently, the exotoxin A of *P. aeruginosa* is used for developing anti-cancer medicines. Immunotoxin produced by fusing specific antibodies with exotoxin A can be targeted to specific types of cells, such as cancer cells, by taking the advantages of specificity associated with the conjugated antibodies. It is expected that the protein synthesis pathway will be blocked in the targeted cells, thereby achieves the purpose of destroying the growth of the particular cell.

In view of various disadvantages derived from conventional aquatic subunit vaccine and the application of *P. aeruginosa* on the genetic engineering, the inventor of this application has devoted to improve it and after studying intensively for many years, provides a novel aquatic subunit vaccine and thus accomplish the invention.

SUMMARY OF THE INVENTION

This invention provides an aquatic subunit vaccine prepared by using genetic engineering techniques to fuse an antigenic protein against fish disease with a receptor binding protein, a translocation protein and a signal peptide such that the antigen can be targeted efficiently and precisely to the effector cell as well as bind and then penetrate the plasma membrane barriers. The antigen from the aquatic subunit vaccine can be presented correctly onto the effector cell and then induce fishes an immunity sufficient to resist viral infection. A number of advantages of vaccines created by recombinant DNA technology include simpler process for mass-production, lower cost of manufacturing, higher purity of produced vaccine, and safety of utilizing the vaccine.

The inventor utilizes the first two functional domains of exotoxin A of *P. aeruginosa*, i.e. the receptor-binding domain (Domain I) and the translocation domain (Domain II), as the PE protein of transporting protein of the antigenic protein of the fish vaccine. In addition, an ER retention signal (i.e. a KDEL signal peptide, whose C terminus has a KDEL signal peptide, and which is recyclable to endoplasmic reticulum) is also conjugated to the designed fish vaccine in order to target specifically the vaccine protein to ER inside the effector cells.

The inventor conjugates the PE protein (containing Domains I and II of the exotoxin A protein, whose amino acid sequence were shown as SEQ ID No: 8) to the N terminus of the fish antigenic protein and the KDEL signal peptide (shown as SEQ ID No: 10) to the C terminus of fish antigenic protein. Therefore, the fish disease-related antigenic protein (thereafter antigenic fusion protein) prepared by fusing PE protein and KDEL signal peptide can be targeted under the action of the PE protein to appropriate cell (i.e. CD8+ T cell) through specific protein-protein interaction between domain I of exotoxin A in the vaccine and receptors on the surface of CD8+ T cell. After the antigenic fusion protein entering the endosome of the CD8+ T cell via endocytosis, it will be processed by protease in the endosome and released into cytoplasm. Then, the KDEL signal peptide will target properly the vaccine protein to bind ER inside the CD8+ T cell for antigen processing and hence induce the effective immunity in fish.

Accordingly, the invention provides an aquatic subunit vaccine comprising an antigenic fusion protein and suitable carrier or adjuvant. The antigenic fusion protein comprises from its N terminus to C terminus sequentially: (1) a receptor binding motif and translocation domain of exotoxin A protein (PE protein); (2) a viral antigenic protein affecting fish disease; and (3) a signal peptide KDEL.

In a preferred embodiment, the PE protein has an amino acid sequence as shown in SEQ ID No: 8, and the KDEL signal peptide has an amino acid sequence as shown in SEQ ID No: 10.

The viral antigenic proteins affecting fish diseases include Infectious Hematopoietic Necrosis Virus's (IHNV) G protein (SEQ ID No: 22) and/or N protein (SEQ ID No: 24), Nervous Necrosis Virus's (NNV) RNA2 protein (SEQ ID No: 26), Grouper Iridovirus's (GIV) Major Capsid Protein (MCP, SEQ ID No: 28) and/or Myristylated Membrane Protein (MMP, SEQ ID No: 30), Spring Viremia of Carp Virus's (SVCV) G protein (SEQ ID No: 32) and/or N protein (SEQ ID No: 34), Viral Hemorrhagic Septicemia Virus's (VHSV) G protein (SEQ ID No: 36) and/or N protein (SEQ ID No: 38), Salmon pancreas disease virus's (PDV) E1 protein (SEQ ID No: 40), E2 protein (SEQ ID No: 42), E3 protein (SEQ ID No: 44), capside protein (CP, SEQ ID No: 46), and/or structural polyprotein (SEQ ID No: 48), and IPNV's VP2 (SEQ ID No: lor SEQ ID No: 4).

In a preferred embodiment, the viral antigenic protein is IPNV's VP2 that has an amino acid sequence encoded in SEQ ID No: 1 or SEQ ID No: 4. In another preferred embodiment, the viral antigenic protein is the antigenic domain of the viral protein VP2 of IPNV, that is the amino acid sequence of amino acids 173 to 431 in the viral protein VP2 of IPNV as shown in SEQ ID No: 3 or SEQ ID No: 6.

The antigenic fusion protein in this invention is created by a gene cloning process as used in usual recombinant DNA technology. The DNA sequence encoding PE protein (as shown in SEQ ID No: 7), the DNA sequence encoding the viral antigenic protein affecting fish disease and DNA sequence encoding the KDEL signal peptide (as shown in SEQ ID No: 9) are cloned in an expression vector system to create an expression plasmid containing DNA sequence encoding antigenic fusion protein. Then, the plasmid is transformed into an expression host cells where protein expression is induced and then the antigenic fusion protein is extracted therefrom.

Viruses affecting fish diseases include Hematopoietic Necrosis Virus's (IHNV) with its G protein (the DNA sequence is shown as SEQ ID No: 21) and/or N protein (the DNA sequence is shown as SEQ ID No: 23), Nervous Necrosis Virus's (NNV) with its RNA2 protein (the DNA sequence is shown as SEQ ID No: 25), Grouper Iridovirus's (GIV) with its Major Capsid Protein (MCP, the DNA sequence is shown as SEQ ID No: 27) and/or Myristylated Membrane Protein (MMP, the DNA sequence is shown as SEQ ID No: 39), Spring Viremia of Carp Virus with its (SVCV) G protein (the DNA sequence is shown as SEQ ID No: 31) and/or N protein (the DNA sequence is shown as SEQ ID No: 33), Viral Hemorrhagic Septicemia Virus's (VHSV) with its G protein (the DNA sequence is shown as SEQ ID No: 35) and/or N protein (the DNA sequence is shown as SEQ ID No: 37), Salmon pancreas disease virus's (PDV) E1 protein (the DNA sequence is shown as SEQ ID No: 39), E2 protein (the DNA sequence is shown as SEQ ID No: 41), E3 protein (the DNA sequence is shown as SEQ ID No: 43), capside protein (CP, the DNA sequence is shown as SEQ ID No: 45), and/or structural polyprotein (the DNA sequence is shown as SEQ ID No: 47), and IPNV with its VP2 (the DNA sequence is shown as SEQ ID No: 2 or SEQ ID No: 5).

In a preferred embodiment, the IPNV antigenic fusion protein has an amino acid sequence of SEQ ID No: 12 or SEQ ID No: 14. The DNA sequence encoding the antigenic fusion protein has a nucleotide sequence of SEQ ID No: 11 or SEQ ID No: 13.

The expression vector system includes but not limited to pET and pGEX vector systems. In a preferred embodiment, the expression vector is pET24a. The expression host may be but not limited to *Escherichia coli*. In a preferred embodiment, the expression host is *E. coli* BL21.

The adjuvant includes but not limited to waterborne adjuvant aluminum hydroxide gel, Alum, Freund's incomplete adjuvant, oil-based adjuvant, water-based adjuvant, or water-in-oil-in-water (W/O/W) adjuvant. In one preferred embodiment, the oil-based adjuvant was used as the adjuvant.

These features and advantages of the present invention will be fully understood and appreciated from the following detailed description of the accompanying drawings.

BRIEF DESCRIPTION OF THE DRAWINGS

FIG. 1*a* to 1*d* are schematic view showing the strategy for constructing the expression vector (pET24-PE-VP2-KDEL) used for the antigenic fusion protein in the aquatic subunit vaccine according to the invention.

FIG. 2 shows amounts of proteins expressed in *E. coli* BL21 by separating with SDS-PAGE electrophoresis and then staining bands with coomassie blue. M: protein marker. FIG. 2*a* Lane 1: *E. coli* BL21 protein extract containing vector pET24a; FIG. 2*a* Lane 2-3: *E. coli* BL21 protein extract containing vector pET24a-VP2-015 (Lane 2, not purified; Lane 3, purified); Lane 4-5: *E. coli* BL21 protein extract containing vector pET24a-VP2-016 (Lane 4: not purified; Lane 5: purified); FIG. 2*b*, Lane 6-7: *E. coli* BL21 protein extract containing plasmid pET24a-PE-VP2-015-KDEL (Lane 6: unpurified; Lane 7: purified); Lane 8-9: *E. coli* BL21 protein extract containing plasmid pET24a-PE-VP2-016-KDEL (Lane 8: unpurified; Lane 9: purified).

FIG. 3 is a graph showing relative percentage of survival (R.P.S.) of each group in Example 3.

DETAILED DESCRIPTION OF THE PREFERRED EMBODIMENT

The aquatic subunit vaccine according to the invention will be illustrated in more detail by reference with an example using a fragment of IPNV viral protein VP2.

EXAMPLE 1

The Construction of pET24-PE-VP2-KDEL Expression Vector for Antigenic Fusion Protein In this example, a fragment of IPNV VP2 was used as the antigen of the aquatic subunit vaccine. A receptor binding motif and the a translocation protein (PE protein) of exotoxin A were conjugated to the N terminus of VP2, as well as a KDEL signal peptide was conjugated to its C terminus, thereby formed the antigenic fusion protein (PE-VP2-KDEL).

The antigenic fusion protein (PE-VP2-KDEL) was created by a gene cloning technology comprising cloning DNA sequences encoding respective proteins into an expression vector to form an expression vector pET24a-PE-VP2-KDEL, and then inducing protein expression.

Figure 1B:
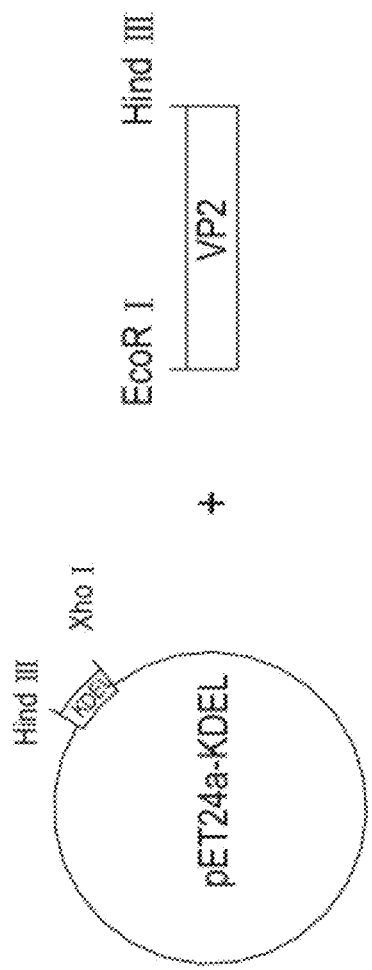
Figure 1C:
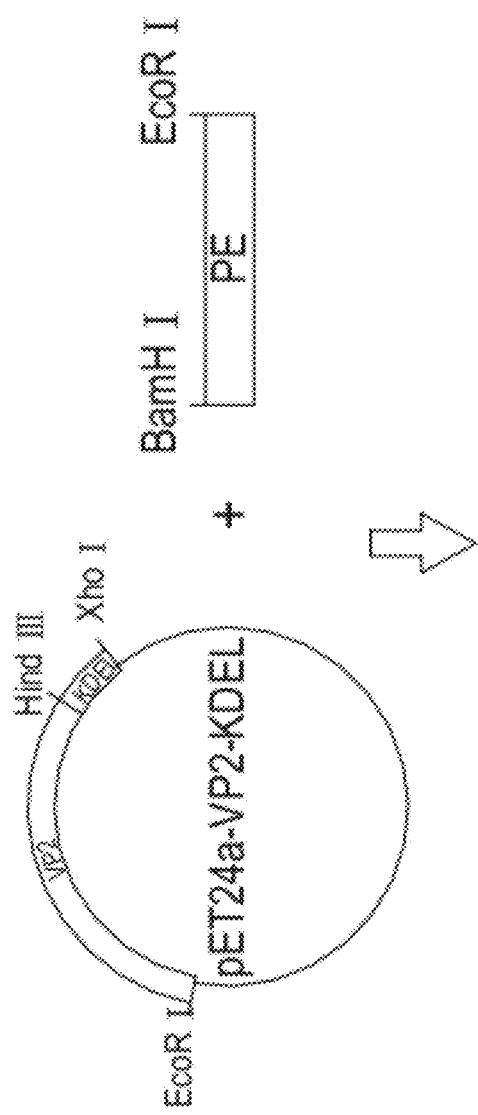
Figure 1D:
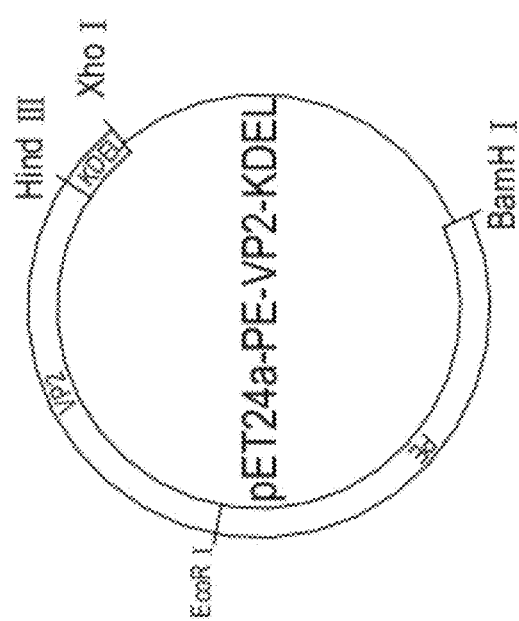
Figure 3:
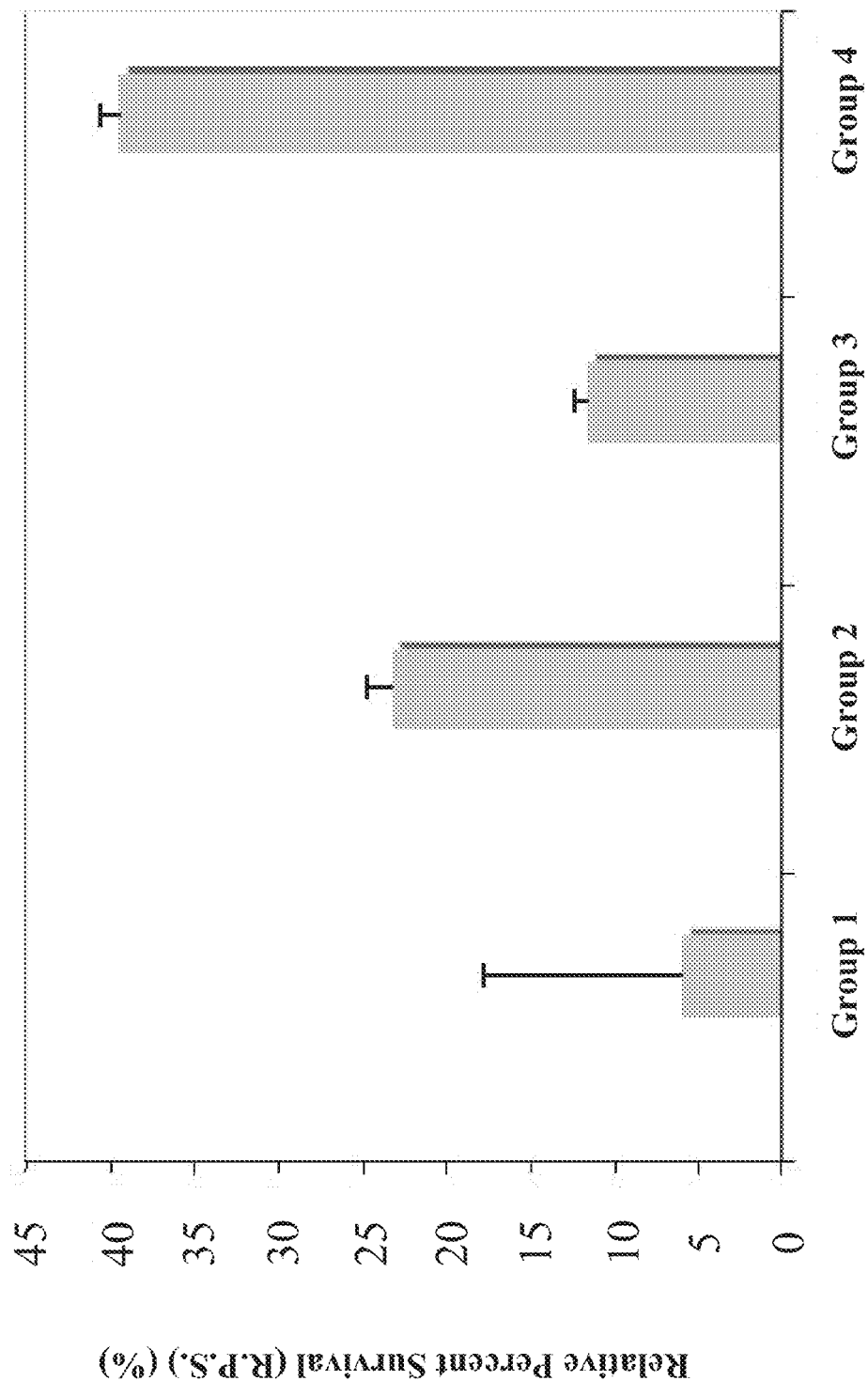

The strategy for constructing the antigenic fusion protein expression vector (24a-PE-VP2-KDEL) is shown in FIG. 1. First, the DNA sequence encoding KDEL signal peptide is cloned into a plasmid pET24a to form plasmid pET24a-KDEL (as shown in FIGS. 1a and 1b). Next, the DNA sequence encoding a sequence of amino acid 173 to amino acid 431 in IPNV VP2 protein is cloned into plasmid pET24a-KDEL to form a construct pET24a-VP2-KDEL (as shown in FIGS. 1b and 1c). Finally, the DNA sequence encoding PE protein is cloned into plasmid pET24a-VP2-KDEL to form a construct pET24a-PE-VP2-KDEL (as shown in FIGS. 1c and 1d).

1. Construction of Plasmid pET24a-KEDL

The DNA sequence encoding KDEL signal peptide (SEQ ID No: 10) is shown as SEQ ID No: 9. The DNA sequence encoding KDEL signal peptide is amplified by a polymerase chain reaction (PCR). The sequence of KEDL-specific primers was shown below:

Forward primer (with Hind III restriction enzyme cleavage site):

(SEQ ID No: 15)
5'-CCC*AAGCTT*CTCAAAAAAGACGAACTGAGAGATGAACTGAAAGA-3'
    Hind III Reverse primer (with Xho I restriction enzyme cleavage site):

(SEQ ID No: 16)
5'-GTC*CTCGAG*TCATTACAGTTCGTCTTTCAGTTCATCT-3'
    Xho I

Conditions for PCR reaction comprised 5 cycles of: 94° C. 3 minutes, 95° C. 1 minute, 55° C. 1 minute, 72° C. 20 seconds; and finally, with 72° C. 1 minute for elongation. PCR product and pET24a vector were subjected to double restriction enzymes digestion with Hind III and Xho I. Thereafter, the digested PCR product and plasmid pET24a were purified, respectively, followed by ligation to clone the PCR product into plasmid pET24a to form a plasmid pET24a-KEDL. Then, the construct pET24a-KEDL was transformed into host cells, *E. coli* RR1, to carry out mass replication. The replicated PCR products were further confirmed by sequencing.

2. Construction of Plasmid pET24a-VP2-KDEL

Two IPNV VP2 proteins, VP2-015 and VP2-016, were used in this example. The full-length sequences of VP2-015 protein and VP2-016 protein were shown as SEQ ID No: 1 and SEQ ID No: 4, respectively. The difference between them was that amino acid residues 217, 221, and 247, were TAT in VP2-015 but PTA in VP2-016.

In this example, the amino acid sequences from amino acid 173 to 431 of VP2-015 and VP2-016 were used as antigens. DNA sequence encoding amino acid 173 to 431 of VP2-015 protein (shown as SEQ ID No: 3) was shown as SEQ ID No: 2 while DNA sequence encoding amino acid 173 to 431 of VP2-016 protein (shown as SEQ ID No: 6) was shown as SEQ ID No: 5. Both DNA sequences were separately amplified by polymerase chain reaction (PCR). VP2 specificity primers were:

Forward primer (with EcoR I restriction enzyme cleavage site):

(SEQ ID No: 17)
5'-CG*GAATTC*CCATACGTCCGCCTAGAGGAC-3'
   EcoR I

Reverse primer (with Hind III restriction enzyme cleavage site):

(SEQ ID No: 18)
5'-CCC*AAGCTT*CGTGATTTCGTTGAAGA-3'
   Hind III

Conditions of PCR reaction comprised 30 cycles of: 94° C. 5 minutes, 94° C. 1 minute, 55° C. 1 minute, and 72° C. 1 minute and finally, 72° C. 7 minutes for an elongation. PCR products and pET24a-KEDL plasmid were subjected to double restriction enzyme digestion (with EcoR 1 and Hind III). The digested PCR products and pET24a-KEDL plasmid were purified separately followed by ligation to form construct pET24a-VP2-015-KEDL and construct pET24a-VP2-016-KEDL. Both constructs pET24a-VP2-KEDL described above were transformed into host cells (*E. coli* RR1) to carry out mass replication. The replicated PCR products were further confirmed by sequencing.

3. Construction of Plasmid pET24a-PE-VP2-KDEL

DNA sequence encoding PE protein (SEQ ID No: 8) was shown as SEQ ID No: 7. The DNA sequence encoding PE protein was amplified by polymerase chain reaction (PCR). The PE-specific primers were:

Forward primer (with BamH I restriction enzyme cleavage site):

(SEQ ID No: 19)
5'-CG*GGATCC*GCCGAAGAAGCTTTCGACCTCTGGAACGAATGC-3'
   BamH I

Reverse primer (with EcoR I restriction enzyme cleavage site):

(SEQ ID No: 20)
5'-CG*GAATTC*GCAGGTCAGGCTCACCAC-3'
   EcoR I

Conditions for PCR reaction comprised 30 cycles of: 94° C. 5 minutes, 95° C. 1 minute, 55° C. 1 minute, and 72° C. 1 and half minutes as well as 72° C. 7 minutes for elongation. PCR products and plasmid pET24a-VP2-015-KEDL or plasmid pET24a-VP2-016-KEDL were subjected to double restriction enzyme digestion (with BamH I and EcoR I). The digested PCR products and plasmids (pET24a-VP2-015-KEDL or pET24a-VP2-016-KEDL) were purified, respectively, followed by ligation to cloning PCR products into plasmid pET24a-VP2-015-KEDL or plasmid pET24a-VP2-016-KEDL to form construct pET24a-PE-VP2-015-KEDL (containing the DNA sequence of PE-VP2-015-KEDL antigenic fusion protein, as indicated in SEQ ID No: 11) and a construct pET24a-PE-VP2-016-KEDL (containing the DNA sequence of PE-VP2-016-KEDL antigenic fusion protein, as shown in SEQ ID No: 13). Constructs pET24a-PE-VP2-015-KEDL or pET24a-PE-VP2-016-KEDL was transformed into host cells (*E. coli* BL21) to carry out mass replication. The replicated PCR products were further confirmed by sequencing.

4. Construction of Plasmid pET24a-VP2

An IPNV's VP2 antigenic protein fragment (absence of PE protein and KDEL signal peptide) was used as a control. The amino acid sequences of amino acid 173 to 431 in VP2-015 and VP2-016, respectively, were used as antigens. The DNA sequence encoding amino acid 173 to amino acid 431 in VP2-015 protein (its amino acid sequence was shown as SEQ ID No: 3) was shown as SEQ ID No: 2. The DNA sequence encoding amino acid 173 to amino acid 431 in VP2-016 protein (its amino acid sequence was shown as SEQ ID No: 6) was shown as SEQ ID No: 5. DNA sequences encoding these VP2 proteins were amplified by polymerase chain reaction (PCR). The VP2-specific primers were:

Forward primer (with EcoR I restriction enzyme cleavage site):

(SEQ ID No: 17)
5'-CC*GAATTC*CCATACGTCCGCCTAGAGGAC-3'
    EcoR I

Reverse primer (with Hind III restriction enzyme cleavage site):

(SEQ ID No: 18)
5'-CCC*AAGCTT*CGTGATTTCGTTGAAGA-3'
    Hind III

Conditions for PCR reaction comprised 30 cycles of: 94° C. 5 minutes, 94° C. 1 minute, 55° C. 1 minute, and 72° C. 1 minute as well as final 72° C. 7 minutes for elongation. PCR products and vector pET24a-KEDL were subjected to double restriction enzyme digestion (with EcoR I and Hind III). The enzyme digested PCR products and vector pET24a were purified separately followed by ligation to clone PCR product into vector pET24a and form constructs pET24a-VP2-015 and pET24a-VP2-016. Both two constructs pET24a-VP2 were transformed into host cells (*E. coli* BL21) to carry out mass replication. The replicated PCR products were further confirmed by sequencing.

EXAMPLE 2

Vaccine Preparation

1. The Expression of Antigenic Fusion Protein

*E. coli* BL21 cells transformed as described above with plasmid pET24a-PE-VP2-015-KEDL or plasmid pET24a-PE-VP2-016-KEDL, or *E. coli* BL21 cells containing plasmid pET24a-PE-VP2-016 or plasmid pET24a-PE-VP2-016 were cultured, respectively, at 37° C. in LB broth containing 50 µg/ml kanamycin overnight. Then, 10 ml of the culture was added into 990 ml fresh LB broth containing 50 µg/ml kanamycin. The diluted cell culture was incubated further at 37° C. by shaking at 250 rpm for 3 hours. Then, 1 ml 1M IPTG (final concentration 1 mM) as an inducer, was added to the culture to induce the expression of the antigenic fusion protein (PE-VP2-015-KEDL whose amino acid sequence was shown as SEQ ID No: 12; or PE-VP2-016-KEDL whose amino acid sequence was shown as SEQ ID No: 14). After IPTG induction, cells were cultured for another three hours and then, harvested by centrifugation at 6,5000×g at 4° C. for 30 minutes. The supernatant was discarded, the cell pellet was recovered and stored at −70° C. till used.

2. Extraction of Antigenic Fusion Protein

The cell pellet described above was resuspended in 200 ml phosphate buffered saline (PBS) and mixed homogeneously. The suspension was centrifuged at 6,5000×g 4° C. for 15 minutes and the supernatant was discarded. The above procedure was repeated at least twice. Thereafter, the cell pellet was resuspended in 100 ml of 1×IB wash Buffer (20 mM Tris-HCl, pH 7.5, 10 mM EDTA, 1% Triton X-100) and placed the cell suspension on ice or at 4° C. to prevent high heat generation during cell breakage. The cells was ruptured then by adding 100 µg/ml of lysozyme into the suspension and incubated at 30° C. for 30 min in combination with sonication or a high speed homogenizer (Polytron) as follows. The lysates were divided into aliquots in 50 ml tubes, mixed by swirling and sonicated on ice with an appropriate tip. Repeat sonication until the solution is no longer viscous. Then, inclusion bodies were collected by centrifugation at 10,000×g for more than 10 min. The supernatant was removed and the pellet was thoroughly resuspended in 0.1 culture volume of 1×IB Wash Buffer. Repeated centrifugation and saved the pellet, until the pellet became white. Again, the pellet was resuspended thoroughly in 0.1 culture volume. Transfer the suspension to a clean centrifuge tube with a known tare weight. The inclusion bodies were collected by centrifugation at 10,000×g for more than 10 min. The supernatant was decanted off and the last trace of liquid was removed by tapping the inverted tube on a paper tower. After thoroughly removing the supernatant, the weight of the inclusion body was measured.

The inclusion body was examined by SDS-PAGE. The result was shown in FIG. 2 *b*, where Land 6 and 7 were antigenic fusion protein PE-VP2-015-KEDL; and Land 8 and 9 were antigenic fusion protein PE-VP2-016-KEDL. The molecular weigh of these antigenic fusion proteins was 71 kDa. The VP2-015 protein fragments as negative control (absence of PE protein and KDEL signal peptide) were shown in FIG. 2*a*, Lane 2 and 3, while VP2-016 protein fragments as negative control (absence of PE protein and KDEL signal peptide) were shown in FIG. 2*a*, Lane 4 and 5. The molecular weights of these protein fragments were 28 kDa.

3. The Preparation of the Vaccine

Antigenic fusion protein PE-VP2-015-KDEL (SEQ ID No: 12), antigenic fusion protein PE-VP2-016-KDEL (SEQ ID No: 14), VP2-015 antigenic protein (SEQ ID No: 3), and VP2-016 antigenic protein (SEQ ID No: 6) were used to prepare monovalent vaccines, respectively. The inclusion bodies containing respective antigenic fusion protein or antigenic protein were dispersed directly in PBS to prepare vaccines each containing 10 µg of respective antigenic fusion protein or antigenic protein. Next, the inclusion bodies were embedded in water-in-oil emulsion and then stored in 4° C.

EXAMPLE 3

Anti-Viral Test in Salmons

The basic information about salmons tested was as followed:

| | |
|---|---|
| Species | Atlantic salmon (*Salmo salar* L.) |
| Strain | Aquagen AS, LR (Low resistance) 06AGHe01 |
| Size | Average 60-90 g |
| Vaccination history | Not previously vaccinated |
| Diseases history | None |

Culture conditions of salmons in the stage of smoltification:

| Salinity | Temp. | Water Quality | Time | Photoperiod | Flow | Density |
|---|---|---|---|---|---|---|
| 0‰ | 8-12° C. | Fresh water | 5 weeks | 12 hours daylight 12 hours darkness | 0.8 l/kg fish pr. min. | Max. 40 kg/m³ |
| 0‰ | 8-12° C. | Fresh water | From week 5 and onwards | 24 hour daylight | 0.8 l/kg fish pr. min. | Max. 40 kg/m³ |

There were four groups plus one control group of salmons used in virus resistant test. Each group had thirty salmons. The prepared vaccines were administrated by intraperitoneal injection (i.p.) into the fishes. The dose of the vaccine was 0.1 ml per fish, which corresponded to 0.1 µg of antigenic fusion protein or VP2 viral protein per fish. The virus resistant test was designed as described below:

Group 1: inoculated with the vaccine containing VP2-015 viral protein
Group 2: inoculated with the vaccine containing PE-VP2-015-KDEL antigenic fusion protein
Group 3: inoculated with the vaccine containing VP2-016 viral protein
Group 4: inoculated with the vaccine containing PE-VP2-016-KDEL antigenic fusion protein
Control: with inoculated PBS solution.

Tests of both experimental and control groups were duplicated. The vaccination was performed at a condition of 900 degree days (temperature times days). For example, if the temperature was 20° C., it should take for 45 days; whereas if the temperature was 10° C., it should take 90 days. Then, salmons tested were transferred to salt water environment for further investigation.

| Salinity | Temp. | Water Quality | Photoperiod | Flow | Density |
|---|---|---|---|---|---|
| 34‰ | 10-12° C. | Salt water | 12 hours daylight 12 hours darkness | 0.5-0.61 l/kg fish pr. min. | Max. 40 $kg/m^3$ |

All groups of fish were fed according to standard protocols. Prior to challenge, fishes were fasted for one day. Naïve fish (20% of fishes tested) were injected intraperitoneally with $1.0\times10^5$ $TCID_{50}$/ml of a virulent strain of IPN virus (serotype Sp and genotype TAT) as the challenge carriers to undergo cohabitation challenge. Fishes of other test groups were moved to seawater tanks. Then, six challenge carriers (20% of the fishes tested) were added to each challenge tank the day after seawater transfer. Thereafter, the mortality of the control and test groups were observed and recorded. The statistic analysis was done when the mortality of the control group was over 60%. Relative percent survival (R.P.S.) was calculated and chi-square test was used for statistic analysis. R.P.S. was calculated according to the formula:

$$R.P.S.=[1-(\text{vaccine mortality}/\text{control mortality})]\times 100\%$$

Next, fishes of test groups were sacrificed and their blood and head kidney samples were collected. The serum samples were collected and frozen for ELISA test. The head kidney samples were used for the virus culture test to reconfirm the death of the fish was caused by IPNV.

Relative percent survival (R.P.S.) of each group was indicated as FIG. 3. It indicated that:

1. The level of survival in the VP2-015-only group (Group 1) was 6%, which is not different significantly from that of the control group (non-vaccinated controls; its R.P.S. was not shown in FIG. 3, but was 0% on calculation based on the above R.P.S. calculation formula).
2. The PE-VP2-015-KDEL immunised fish (Group 2) had an RPS of 23% and indicated a significantly increased level of protection (RPS value) compared to the VP-015-only group (Group 1) ($p<0.01$).
3. For the VP2-016-only (Group 3) immunised fish, there was a significant protection effect (RPS value=12%; $p<0.05$) in the vaccinated fish compared to non-vaccinated controls.
4. For the PE-VP2-016-KDEL (Group 4) immunised fish, the obtained RPS value was 39%, and was different significantly from the VP2-016 only group ($p<0.01$).

Compared with other traditional technologies, advantages of the inventive aquatic subunit vaccine are listed in the following:

1. The inventive subunit vaccine is prepared based upon recombinant DNA technology by fusing the receptor binding motif and the translocation domain of *Pseudomonas aeruginosa* exotoxin A, and the KDEL signal peptide, thereby it can enhance the expression of vaccine protein within host cells, and result in better immunological effect and protection of immunized fish.
2. In addition, the novel vaccine according to the invention is a subunit vaccine and its manufacturing process by gene cloning has advantages of being a simple process for mass-production, lower production cost, higher purity of vaccine products, and safety of using the vaccine.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A subunit vaccine for aquaculture against Infectious pancreatic Necrosis (IPN), comprising an antigenic fused protein and a pharmaceutically acceptable carrier, wherein the antigenic fused protein comprises from amino terminal to carboxyl terminal of:
   a receptor binding domain and a translocation domain of *Pseudomonas aeruginosa* exotoxin A;
   a viral antigenic protein of IPN; and
   a signal peptide comprising the amino acid sequence of SEQ ID No: 10.

2. A subunit vaccine for aquaculture as recited in claim 1, wherein the receptor binding domain and the translocation domain of the *Pseudomonas aeruginosa* exotoxin A comprise the amino acid sequence of SEQ ID No: 8.

3. A subunit vaccine for aquaculture as recited in claim 1, wherein the viral antigenic protein is derived from viral protein VP2 of IPNV and comprises the amino acid sequence as shown in SEQ ID No: 1.

4. A subunit vaccine for aquaculture as recited in claim 1, wherein the viral antigenic protein is derived from the amino acid sequence of amino acid 173 to 431 of viral protein VP2 of IPNV and comprises the amino acid sequence as shown in SEQ ID No: 3.

5. A subunit vaccine for aquaculture as recited in claim 1, wherein the viral antigenic protein is derived from viral protein VP2 of IPNV and comprises the amino acid sequence as shown in SEQ ID No: 4.

6. A subunit vaccine for aquaculture as recited in claim 1, wherein the viral antigenic protein is derived from the amino acid sequence of amino acid 173 to 431 of viral protein VP2 of IPNV and comprises the amino acid sequence as shown in SEQ ID No: 6.

7. A subunit vaccine for aquaculture as recited in claim 1, wherein the antigenic fused protein comprises the sequence of SEQ ID No: 12.

8. A subunit vaccine for aquaculture as recited in claim 1, wherein the antigenic fused protein comprises the sequence of SEQ ID No: 14.

9. A subunit vaccine for aquaculture as recited in claim 1, wherein the subunit vaccine further comprises an a adjuvant, wherein the adjuvant is one selected from the group consisting of waterborne adjuvant aluminum hydroxide gel, Alum, Freund's incomplete adjuvant, oil-based adjuvant, water-based adjuvant, and water-in-oil-in-water (W/O/W) adjuvant.

* * * * *

SEQUENCE LISTING

<160> NUMBER OF SEQ ID NOS: 48

<210> SEQ ID NO 1
<211> LENGTH: 972
<212> TYPE: PRT
<213> ORGANISM: Infectious Pancreatic Necrosis Virus (IPNV)
<300> PUBLICATION INFORMATION:
<308> DATABASE ACCESSION NUMBER: Genbank/AAQ75357.1
<309> DATABASE ENTRY DATE: 2004-04-16

<400> SEQUENCE: 1

```
Met Asn Thr Asn Lys Ala Thr Ala Thr Tyr Leu Lys Ser Ile Met Leu
1               5                   10                  15

Pro Glu Thr Gly Pro Ala Ser Ile Pro Asp Asp Ile Thr Glu Arg His
            20                  25                  30

Ile Leu Lys Gln Glu Thr Ser Ser Tyr Asn Leu Glu Val Ser Glu Ser
        35                  40                  45

Gly Ser Gly Ile Leu Val Cys Phe Pro Gly Ala Pro Gly Ser Arg Ile
    50                  55                  60

Gly Ala His Tyr Arg Trp Asn Ala Asn Gln Thr Gly Leu Glu Phe Asp
65                  70                  75                  80

Gln Trp Leu Glu Thr Ser Gln Asp Leu Lys Lys Ala Phe Asn Tyr Gly
                85                  90                  95

Arg Leu Ile Ser Arg Lys Tyr Asp Ile Gln Ser Ser Thr Leu Pro Ala
            100                 105                 110

Gly Leu Tyr Ala Leu Asn Gly Thr Leu Asn Ala Ala Thr Phe Glu Gly
        115                 120                 125

Ser Leu Ser Glu Val Glu Ser Leu Thr Tyr Asn Ser Leu Met Ser Leu
    130                 135                 140

Thr Thr Asn Pro Gln Asp Lys Val Asn Asn Gln Leu Val Thr Lys Gly
145                 150                 155                 160

Val Thr Val Leu Asn Leu Pro Thr Gly Phe Asp Lys Pro Tyr Val Arg
                165                 170                 175

Leu Glu Asp Glu Thr Pro Gln Gly Leu Gln Ser Met Asn Gly Ala Lys
            180                 185                 190

Met Arg Cys Thr Ala Ala Ile Ala Pro Arg Arg Tyr Glu Ile Asp Leu
        195                 200                 205

Pro Ser Gln Arg Leu Pro Pro Val Thr Ala Thr Gly Ala Leu Thr Thr
    210                 215                 220

Leu Tyr Glu Gly Asn Ala Asp Ile Val Asn Ser Thr Thr Val Thr Gly
225                 230                 235                 240

Asp Ile Asn Phe Ser Leu Thr Glu Gln Pro Ala Val Glu Thr Lys Phe
                245                 250                 255

Asp Phe Gln Leu Asp Phe Met Gly Leu Asp Asn Asp Val Pro Val Val
            260                 265                 270

Thr Val Val Ser Ser Val Leu Ala Thr Asn Asp Asn Tyr Arg Gly Val
        275                 280                 285

Ser Ala Lys Met Thr Gln Ser Ile Pro Thr Glu Asn Ile Thr Lys Pro
    290                 295                 300

Ile Thr Arg Val Lys Leu Ser Tyr Lys Ile Asn Gln Gln Thr Ala Ile
305                 310                 315                 320

Gly Asn Val Ala Thr Leu Gly Thr Met Gly Pro Ala Ser Val Ser Phe
                325                 330                 335

Ser Ser Gly Asn Gly Asn Val Pro Gly Val Leu Arg Pro Ile Thr Leu
            340                 345                 350
```

```
Val Ala Tyr Glu Lys Met Thr Pro Leu Ser Ile Leu Thr Val Ala Gly
            355                 360                 365
Val Ser Asn Tyr Glu Leu Ile Pro Asn Pro Glu Leu Leu Lys Asn Met
        370                 375                 380
Val Thr Arg Tyr Gly Lys Tyr Asp Pro Glu Gly Leu Asn Tyr Ala Lys
385                 390                 395                 400
Met Ile Leu Ser His Arg Glu Glu Leu Asp Ile Arg Thr Val Trp Arg
                405                 410                 415
Thr Glu Glu Tyr Lys Glu Arg Thr Arg Val Phe Asn Glu Ile Thr Asp
            420                 425                 430
Phe Ser Ser Asp Leu Pro Thr Ser Lys Ala Trp Gly Trp Arg Asp Ile
        435                 440                 445
Val Arg Gly Ile Arg Lys Val Ala Ala Pro Val Leu Ser Thr Leu Phe
    450                 455                 460
Pro Met Ala Ala Pro Leu Ile Gly Met Ala Asp Gln Phe Ile Gly Asp
465                 470                 475                 480
Leu Thr Lys Thr Asn Ala Ala Gly Gly Arg Tyr His Ser Met Ala Ala
                485                 490                 495
Gly Gly Arg Tyr Lys Asp Val Leu Glu Ser Trp Ala Ser Gly Gly Pro
            500                 505                 510
Asp Gly Lys Phe Ser Arg Ala Leu Lys Asn Arg Leu Glu Ser Ala Asn
        515                 520                 525
Tyr Glu Glu Val Glu Leu Pro Pro Ser Lys Gly Val Ile Val Pro
    530                 535                 540
Val Val His Thr Val Lys Ser Ala Pro Gly Glu Ala Phe Gly Ser Leu
545                 550                 555                 560
Ala Ile Ile Ile Pro Gly Glu Tyr Pro Glu Leu Leu Asp Ala Asn Gln
                565                 570                 575
Gln Val Leu Ser His Phe Ala Asn Asp Thr Gly Ser Val Trp Gly Ile
            580                 585                 590
Gly Glu Asp Ile Pro Phe Glu Gly Asp Asn Met Cys Tyr Thr Ala Leu
        595                 600                 605
Pro Leu Lys Glu Ile Lys Arg Asn Gly Asn Ile Val Val Glu Lys Ile
    610                 615                 620
Phe Ala Gly Pro Ile Met Gly Pro Ser Ala Gln Leu Gly Leu Ser Leu
625                 630                 635                 640
Leu Val Asn Asp Ile Glu Asp Gly Val Pro Arg Met Val Phe Thr Gly
                645                 650                 655
Glu Ile Ala Asp Asp Glu Glu Thr Ile Ile Pro Ile Cys Gly Val Asp
            660                 665                 670
Ile Lys Ala Ile Ala Ala His Glu Gln Gly Leu Pro Leu Ile Gly Asn
        675                 680                 685
Gln Pro Gly Val Asp Glu Glu Val Arg Asn Thr Ser Leu Ala Ala His
    690                 695                 700
Leu Ile Gln Thr Gly Thr Leu Pro Val Gln Arg Ala Lys Gly Ser Asn
705                 710                 715                 720
Lys Arg Ile Lys Tyr Leu Gly Glu Leu Met Ala Ser Asn Ala Ser Gly
                725                 730                 735
Met Asp Glu Glu Leu Gln Arg Leu Leu Asn Ala Thr Met Ala Arg Ala
            740                 745                 750
Lys Glu Val Gln Asp Ala Glu Ile Tyr Lys Leu Leu Lys Leu Met Ala
        755                 760                 765
Trp Thr Arg Lys Asn Asp Leu Thr Asp His Met Tyr Glu Trp Ser Lys
```

```
                    770                 775                 780
Glu Asp Pro Asp Ala Leu Lys Phe Gly Lys Leu Ile Ser Thr Pro Pro
785                 790                 795                 800

Lys Arg Pro Glu Lys Pro Lys Gly Pro Asp Gln His His Ala Gln Glu
                805                 810                 815

Ala Arg Ala Thr Arg Ile Ser Leu Asp Ala Val Arg Ala Gly Ala Asp
                820                 825                 830

Phe Ala Thr Pro Glu Trp Val Ala Leu Asn Asn Tyr Arg Gly Pro Ser
                835                 840                 845

Pro Gly Gln Phe Lys Tyr Tyr Leu Ile Thr Gly Arg Glu Pro Glu Pro
                850                 855                 860

Gly Asp Glu Tyr Glu Asp Tyr Ile Lys Gln Pro Ile Val Lys Pro Thr
865                 870                 875                 880

Asp Met Asn Lys Ile Arg Arg Leu Ala Asn Ser Val Tyr Gly Leu Pro
                885                 890                 895

His Gln Glu Pro Ala Pro Glu Glu Phe Tyr Asp Ala Val Ala Ala Val
                900                 905                 910

Phe Ala Gln Asn Gly Gly Arg Gly Pro Asp Gln Asp Gln Met Gln Asp
                915                 920                 925

Leu Arg Glu Leu Ala Arg Gln Met Lys Arg Arg Pro Arg Asn Ala Asp
930                 935                 940

Ala Pro Arg Arg Thr Arg Ala Pro Ala Glu Pro Ala Pro Pro Gly Arg
945                 950                 955                 960

Ser Arg Phe Thr Pro Ser Gly Asp Asn Ala Glu Val
                965                 970

<210> SEQ ID NO 2
<211> LENGTH: 777
<212> TYPE: DNA
<213> ORGANISM: Infectious Pancreatic Necrosis Virus (IPNV)
<300> PUBLICATION INFORMATION:
<308> DATABASE ACCESSION NUMBER: Genbank/AY379740
<309> DATABASE ENTRY DATE: 2004-04-16
<313> RELEVANT RESIDUES IN SEQ ID NO: (635)...(1411)

<400> SEQUENCE: 2
ccatacgtcc gcctagagga cgagacaccc cagggtctcc agtcaatgaa cggggccaag      60
atgaggtgca cagctgcaat tgcaccgcgg aggtacgaga tcgacctccc atcccaacgc     120
ctaccccccg ttactgcgac aggagccctc accactctct acgagggaaa cgccgacatc     180
gtcaactcca cgacagtgac gggagacata aacttcagtc tgacagaaca acccgcagtc     240
gagaccaagt tcgacttcca gctggacttc atgggccttg acaacgacgt cccagttgtc     300
acagtggtca gctccgtgct ggccacaaat gacaactaca gaggagtctc agccaagatg     360
acccagtcca tcccgaccga gaacatcaca aagccgatca ccagggtcaa gctgtcatac     420
aagatcaacc agcagacggc aatcggcaac gtcgccaccc tgggcacaat gggtccagca     480
tccgtctcct tctcatcagg gaacggaaat gtccccggcg tgctcagacc aatcacactg     540
gtggcctatg agaagatgac accgctgtcc atcctgaccg tagctggagt gtccaactac     600
gagctgatcc caaacccaga actcctaaag aacatggtga cacgctatgg caagtacgac     660
cccgaaggtc tcaactatgc caagatgatc ctgtcccaca gggaagagct ggacatcagg     720
acagtgtgga ggacagagga gtacaaggag aggaccagag tcttcaacga aatcacg       777

<210> SEQ ID NO 3
<211> LENGTH: 259
<212> TYPE: PRT
```

-continued

<213> ORGANISM: Infectious Pancreatic Necrosis Virus (IPNV)
<300> PUBLICATION INFORMATION:
<308> DATABASE ACCESSION NUMBER: Genbank/AAQ75357.1
<309> DATABASE ENTRY DATE: 2004-04-16
<313> RELEVANT RESIDUES IN SEQ ID NO: (173)...(431)

<400> SEQUENCE: 3

```
Pro Tyr Val Arg Leu Glu Asp Glu Thr Pro Gln Gly Leu Gln Ser Met
1               5                   10                  15

Asn Gly Ala Lys Met Arg Cys Thr Ala Ala Ile Ala Pro Arg Arg Tyr
            20                  25                  30

Glu Ile Asp Leu Pro Ser Gln Arg Leu Pro Pro Val Thr Ala Thr Gly
        35                  40                  45

Ala Leu Thr Thr Leu Tyr Glu Gly Asn Ala Asp Ile Val Asn Ser Thr
    50                  55                  60

Thr Val Thr Gly Asp Ile Asn Phe Ser Leu Thr Glu Gln Pro Ala Val
65                  70                  75                  80

Glu Thr Lys Phe Asp Phe Gln Leu Asp Phe Met Gly Leu Asp Asn Asp
                85                  90                  95

Val Pro Val Val Thr Val Val Ser Ser Val Leu Ala Thr Asn Asp Asn
            100                 105                 110

Tyr Arg Gly Val Ser Ala Lys Met Thr Gln Ser Ile Pro Thr Glu Asn
        115                 120                 125

Ile Thr Lys Pro Ile Thr Arg Val Lys Leu Ser Tyr Lys Ile Asn Gln
    130                 135                 140

Gln Thr Ala Ile Gly Asn Val Ala Thr Leu Gly Thr Met Gly Pro Ala
145                 150                 155                 160

Ser Val Ser Phe Ser Ser Gly Asn Gly Asn Val Pro Gly Val Leu Arg
                165                 170                 175

Pro Ile Thr Leu Val Ala Tyr Glu Lys Met Thr Pro Leu Ser Ile Leu
            180                 185                 190

Thr Val Ala Gly Val Ser Asn Tyr Glu Leu Ile Pro Asn Pro Glu Leu
        195                 200                 205

Leu Lys Asn Met Val Thr Arg Tyr Gly Lys Tyr Asp Pro Glu Gly Leu
    210                 215                 220

Asn Tyr Ala Lys Met Ile Leu Ser His Arg Glu Glu Leu Asp Ile Arg
225                 230                 235                 240

Thr Val Trp Arg Thr Glu Glu Tyr Lys Glu Arg Thr Arg Val Phe Asn
                245                 250                 255

Glu Ile Thr
```

<210> SEQ ID NO 4
<211> LENGTH: 972
<212> TYPE: PRT
<213> ORGANISM: Infectious Pancreatic Necrosis Virus (IPNV)
<300> PUBLICATION INFORMATION:
<308> DATABASE ACCESSION NUMBER: Genbank/AAQ75360.1
<309> DATABASE ENTRY DATE: 2004-04-16

<400> SEQUENCE: 4

```
Met Asn Thr Asn Lys Ala Thr Ala Thr Tyr Leu Lys Ser Ile Met Leu
1               5                   10                  15

Pro Glu Thr Gly Pro Ala Ser Ile Pro Asp Asp Ile Thr Glu Arg His
            20                  25                  30

Ile Leu Lys Gln Glu Thr Ser Ser Tyr Asn Leu Glu Val Ser Glu Ser
        35                  40                  45

Gly Ser Gly Ile Leu Val Cys Phe Pro Gly Ala Pro Gly Ser Arg Ile
    50                  55                  60
```

```
Gly Ala His Tyr Arg Trp Asn Ala Asn Gln Thr Gly Leu Glu Phe Asp
 65                  70                  75                  80

Gln Trp Leu Glu Thr Ser Gln Asp Leu Lys Lys Ala Phe Asn Tyr Gly
                 85                  90                  95

Arg Leu Ile Ser Arg Lys Tyr Asp Ile Gln Ser Ser Thr Leu Pro Ala
            100                 105                 110

Gly Leu Tyr Ala Leu Asn Gly Thr Leu Asn Ala Thr Phe Glu Gly
        115                 120                 125

Ser Leu Ser Glu Val Glu Ser Leu Thr Tyr Asn Ser Leu Met Ser Leu
        130                 135                 140

Thr Thr Asn Pro Gln Asp Lys Val Asn Asn Gln Leu Val Thr Lys Gly
145                 150                 155                 160

Val Thr Val Leu Asn Leu Pro Thr Gly Phe Asp Lys Pro Tyr Val Arg
                165                 170                 175

Leu Glu Asp Glu Thr Pro Gln Gly Leu Gln Ser Met Asn Gly Ala Lys
            180                 185                 190

Met Arg Cys Thr Ala Ala Ile Ala Pro Arg Arg Tyr Glu Ile Asp Leu
        195                 200                 205

Pro Ser Gln Arg Leu Pro Pro Val Pro Ala Thr Gly Thr Leu Thr Thr
        210                 215                 220

Leu Tyr Glu Gly Asn Ala Asp Ile Val Asn Ser Thr Val Thr Gly
225                 230                 235                 240

Asp Ile Asn Phe Ser Leu Ala Glu Gln Pro Ala Asn Glu Thr Lys Phe
                245                 250                 255

Asp Phe Gln Leu Asp Phe Met Gly Leu Asp Asn Asp Val Pro Val Val
            260                 265                 270

Thr Val Val Ser Ser Val Leu Ala Thr Asn Asp Asn Tyr Arg Gly Val
        275                 280                 285

Ser Ala Lys Met Thr Gln Ser Ile Pro Thr Glu Asn Ile Thr Lys Pro
        290                 295                 300

Ile Thr Arg Val Lys Leu Ser Tyr Lys Ile Asn Gln Gln Thr Ala Ile
305                 310                 315                 320

Gly Asn Val Ala Thr Leu Gly Thr Met Gly Pro Ala Ser Val Ser Phe
                325                 330                 335

Ser Ser Gly Asn Gly Asn Val Pro Gly Val Leu Arg Pro Ile Thr Leu
            340                 345                 350

Val Ala Tyr Glu Lys Met Thr Pro Leu Ser Ile Leu Thr Val Ala Gly
        355                 360                 365

Val Ser Asn Tyr Glu Leu Ile Pro Asn Pro Glu Leu Leu Lys Asn Met
        370                 375                 380

Val Thr Arg Tyr Gly Lys Tyr Asp Pro Glu Gly Leu Asn Tyr Ala Lys
385                 390                 395                 400

Met Ile Leu Ser His Arg Glu Glu Leu Asp Ile Arg Thr Val Trp Arg
                405                 410                 415

Thr Glu Glu Tyr Lys Glu Arg Thr Arg Val Phe Asn Glu Ile Thr Asp
            420                 425                 430

Phe Ser Ser Asp Leu Pro Thr Ser Lys Ala Trp Gly Trp Arg Asp Ile
        435                 440                 445

Val Arg Gly Ile Arg Lys Val Ala Ala Pro Val Leu Ser Thr Leu Phe
        450                 455                 460

Pro Met Ala Ala Pro Leu Ile Gly Met Ala Asp Gln Phe Ile Gly Asp
465                 470                 475                 480

Leu Thr Lys Thr Asn Ala Ala Gly Gly Arg Tyr His Ser Met Ala Ala
```

```
                        485                 490                 495
Gly Gly Arg Tyr Lys Asp Val Leu Glu Ser Trp Ala Ser Gly Gly Pro
                500                 505                 510
Asp Gly Lys Phe Ser Arg Ala Leu Lys Asn Arg Leu Glu Ser Ala Asn
            515                 520                 525
Tyr Glu Glu Val Glu Leu Pro Pro Ser Lys Gly Val Ile Val Pro
        530                 535                 540
Val Val His Thr Val Lys Ser Ala Pro Gly Ala Phe Gly Ser Leu
545                 550                 555                 560
Ala Ile Ile Ile Pro Gly Glu Tyr Pro Glu Leu Leu Asp Ala Asn Gln
                565                 570                 575
Gln Val Leu Ser His Phe Ala Asn Asp Thr Gly Ser Val Trp Gly Ile
            580                 585                 590
Gly Glu Asp Ile Pro Phe Glu Gly Asp Asn Met Cys Tyr Thr Ala Leu
        595                 600                 605
Pro Leu Lys Glu Ile Lys Arg Asn Gly Asn Ile Val Val Glu Lys Ile
        610                 615                 620
Phe Ala Gly Pro Ile Met Gly Pro Ser Ala Gln Leu Gly Leu Ser Leu
625                 630                 635                 640
Leu Val Asn Asp Ile Glu Asp Gly Val Pro Arg Met Val Phe Thr Gly
                645                 650                 655
Glu Ile Ala Asp Asp Glu Glu Thr Ile Ile Pro Ile Cys Gly Val Asp
            660                 665                 670
Ile Lys Ala Ile Ala Ala His Glu Gln Gly Leu Pro Leu Ile Gly Asn
        675                 680                 685
Gln Pro Gly Val Asp Glu Glu Val Arg Asn Thr Ser Leu Ala Ala His
        690                 695                 700
Leu Ile Gln Thr Gly Thr Leu Pro Val Gln Arg Ala Lys Gly Ser Asn
705                 710                 715                 720
Lys Arg Ile Lys Tyr Leu Gly Glu Leu Met Ala Ser Asn Ala Ser Gly
                725                 730                 735
Met Asp Glu Glu Leu Gln Arg Leu Leu Asn Ala Thr Met Ala Arg Ala
            740                 745                 750
Lys Glu Val Gln Asp Ala Glu Ile Tyr Lys Leu Leu Lys Leu Met Ala
        755                 760                 765
Trp Thr Arg Lys Asn Asp Leu Thr Asp His Met Tyr Glu Trp Ser Lys
        770                 775                 780
Glu Asp Pro Asp Ala Leu Lys Phe Gly Lys Leu Ile Ser Thr Pro Pro
785                 790                 795                 800
Lys Arg Pro Glu Lys Pro Lys Gly Pro Asp Gln His His Ala Gln Glu
                805                 810                 815
Ala Arg Ala Thr Arg Ile Ser Leu Asp Ala Val Arg Ala Gly Ala Asp
            820                 825                 830
Phe Ala Thr Pro Glu Trp Val Ala Leu Asn Asn Tyr Arg Gly Pro Ser
        835                 840                 845
Pro Gly Gln Phe Lys Tyr Tyr Leu Ile Thr Gly Arg Glu Pro Glu Pro
        850                 855                 860
Gly Asp Glu Tyr Glu Asp Tyr Ile Lys Gln Pro Ile Val Lys Pro Thr
865                 870                 875                 880
Asp Met Asn Lys Ile Arg Arg Leu Ala Asn Ser Val Tyr Gly Leu Pro
                885                 890                 895
His Gln Glu Pro Ala Pro Glu Glu Phe Tyr Asp Ala Val Ala Ala Val
            900                 905                 910
```

```
Phe Ala Gln Asn Gly Gly Arg Gly Pro Asp Gln Asp Gln Met Gln Asp
            915                 920                 925

Leu Arg Glu Leu Ala Arg Gln Met Lys Arg Arg Pro Arg Asn Ala Asp
        930                 935                 940

Ala Pro Arg Arg Thr Arg Ala Pro Ala Glu Pro Ala Pro Pro Gly Arg
945                 950                 955                 960

Ser Arg Phe Thr Pro Ser Gly Asp Asn Ala Glu Val
            965                 970

<210> SEQ ID NO 5
<211> LENGTH: 777
<212> TYPE: DNA
<213> ORGANISM: Infectious Pancreatic Necrosis Virus (IPNV)
<300> PUBLICATION INFORMATION:
<308> DATABASE ACCESSION NUMBER: Genbank/AY379742
<309> DATABASE ENTRY DATE: 2004-04-16
<313> RELEVANT RESIDUES IN SEQ ID NO: (635)...(1411)

<400> SEQUENCE: 5
ccatacgtcc gcctagagga cgagacaccc cagggtctcc agtcaatgaa cggggccaag      60
atgaggtgca cagctgcaat tgcaccgcgg aggtacgaga tcgacctccc atcccaacgc     120
ctaccccccg ttcctgcgac aggaaccctc accactctct acgagggaaa cgccgacatc     180
gtcaactcca acagtgac gggagacata aacttcagtc tggcagaaca acccgcaaac      240
gagaccaagt tcgacttcca gctggacttc atgggccttg acaacgacgt cccagttgtc     300
acagtggtca gctccgtgct ggccacagac gacaactaca gaggagtctc agccaagatg     360
acccagtcca tcccaaccga gaacatcaca aagccgatca ccagggtcaa gctgtcatac     420
aagatcaacc agcagacaga aatcggcaac ttcgccaccc tgggcacaat gggtccagca     480
tccgtctcct tctcatcagg gaacggaaat gtccccggcg tgctcagacc aatcacactg     540
gtggcctatg agaagatgac accgctgtcc atcctgaccg tagctggagt gtccaactac     600
gagctgatcc caaacccaga actcctcaag aacatggtga cacgctatgg caagtacgac     660
cccgaaggtc tcaactatgc caagatgatc ctgtcccaca gggaggagct ggacatcagg     720
acagtgtgga ggacagagga gtacaaggag aggaccagag tcttcaacga aatcacg     777

<210> SEQ ID NO 6
<211> LENGTH: 259
<212> TYPE: PRT
<213> ORGANISM: Infectious Pancreatic Necrosis Virus (IPNV)
<300> PUBLICATION INFORMATION:
<308> DATABASE ACCESSION NUMBER: Genbank/AAQ75360.1
<309> DATABASE ENTRY DATE: 2004-04-16
<313> RELEVANT RESIDUES IN SEQ ID NO: (173)...(431)

<400> SEQUENCE: 6

Pro Tyr Val Arg Leu Glu Asp Glu Thr Pro Gln Gly Leu Gln Ser Met
1                5                  10                  15

Asn Gly Ala Lys Met Arg Cys Thr Ala Ala Ile Ala Pro Arg Arg Tyr
            20                  25                  30

Glu Ile Asp Leu Pro Ser Gln Arg Leu Pro Pro Val Pro Ala Thr Gly
        35                  40                  45

Thr Leu Thr Thr Leu Tyr Glu Gly Asn Ala Asp Ile Val Asn Ser Thr
    50                  55                  60

Thr Val Thr Gly Asp Ile Asn Phe Ser Leu Ala Glu Gln Pro Ala Asn
65                  70                  75                  80

Glu Thr Lys Phe Asp Phe Gln Leu Asp Phe Met Gly Leu Asp Asn Asp
                85                  90                  95
```

-continued

```
Val Pro Val Val Thr Val Ser Ser Val Leu Ala Thr Asn Asp Asn
            100                 105                 110

Tyr Arg Gly Val Ser Ala Lys Met Thr Gln Ser Ile Pro Thr Glu Asn
            115                 120                 125

Ile Thr Lys Pro Ile Thr Arg Val Lys Leu Ser Tyr Lys Ile Asn Gln
        130                 135                 140

Gln Thr Ala Ile Gly Asn Val Ala Thr Leu Gly Thr Met Gly Pro Ala
145                 150                 155                 160

Ser Val Ser Phe Ser Ser Gly Asn Gly Asn Val Pro Gly Val Leu Arg
                165                 170                 175

Pro Ile Thr Leu Val Ala Tyr Glu Lys Met Thr Pro Leu Ser Ile Leu
            180                 185                 190

Thr Val Ala Gly Val Ser Asn Tyr Glu Leu Ile Pro Asn Pro Glu Leu
        195                 200                 205

Leu Lys Asn Met Val Thr Arg Tyr Gly Lys Tyr Asp Pro Glu Gly Leu
    210                 215                 220

Asn Tyr Ala Lys Met Ile Leu Ser His Arg Glu Glu Leu Asp Ile Arg
225                 230                 235                 240

Thr Val Trp Arg Thr Glu Glu Tyr Lys Glu Arg Thr Arg Val Phe Asn
                245                 250                 255

Glu Ile Thr
```

<210> SEQ ID NO 7
<211> LENGTH: 1116
<212> TYPE: DNA
<213> ORGANISM: Pseudomonas aeruginosa
<300> PUBLICATION INFORMATION:
<308> DATABASE ACCESSION NUMBER: Genbank/K01397
<309> DATABASE ENTRY DATE: 2002-02-11
<313> RELEVANT RESIDUES IN SEQ ID NO: (821)...(1936)

<400> SEQUENCE: 7

```
gccgaagaag ctttcgacct ctggaacgaa tgcgccaaag cctgcgtgct cgacctcaag      60
gacggcgtgc gttccagccg catgagcgtc gacccggcca tcgccgacac caacggccag     120
ggcgtgctgc actactccat ggtcctggag gcggcaacg acgcgctcaa gctggccatc     180
gacaacgccc tcagcatcac cagcgacggc ctgaccatcc gcctcgaagg cggcgtcgag     240
ccgaacaagc cggtgcgcta cagctacacg cgccaggcgc gcggcagttg gtcgctgaac     300
tggctggtac cgatcggcca cgagaagccc tcgaacatca aggtgttcat ccacgaactg     360
aacgccggca accagctcag ccacatgtcg ccgatctaca ccaccgagat gggcgacgag     420
ttgctagcga agctggcgcg cgatgccacc ttcttcgtca gggcgcacga gagcaacgag     480
atgcagccga cgctcgccat cagccatgcc ggggtcagcg tggtcatggc ccagacccag     540
ccgcgccggg aaaagcgctg gagcgaatgg gccagcggca aggtgttgtg cctgctcgac     600
ccgctggacg ggtctacaa ctacctcgcc cagcaacgct gcaacctcga cgatacctgg     660
gaaggcaaga tctaccgggt gctcgccggc aacccggcga agcatgacct ggacatcaaa     720
cccacggtca tcagtcatcg cctgcacttt cccgagggcg gcagcctggc cgcgctgacc     780
gcgcaccagg cttgccacct gccgctggag actttcaccc gtcatcgcca gccgcgcggc     840
tgggaacaac tggagcagtg cggctatccg gtgcagcggc tggtcgccct ctacctggcg     900
gcgcggctgt cgtggaacca ggtcgaccag gtgatccgca acgccctggc cagcccggc     960
agcggcggcg acctaggcga agcgatccgc gagcagccgg agcaggcccg tctggccctg    1020
accctggccg ccgccgagag cgagcgcttc atccggcagg gcaccggcaa cgacgaggcc    1080
```
ggcgcggcca acgccgacgt ggtgagcctg acctgc                        1116

<210> SEQ ID NO 8
<211> LENGTH: 372
<212> TYPE: PRT
<213> ORGANISM: Pseudomonas aeruginosa

<400> SEQUENCE: 8

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Thr Glu Met Gly Asp Glu Leu Leu Ala Lys
130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Ile Arg
            340                 345                 350

Gln Gly Thr Gly Asn Asp Glu Ala Gly Ala Ala Asn Ala Asp Val Val
        355                 360                 365

Ser Leu Thr Cys

-continued

370

<210> SEQ ID NO 9
<211> LENGTH: 48
<212> TYPE: DNA
<213> ORGANISM: artificial sequence
<220> FEATURE:
<223> OTHER INFORMATION: The DNA sequence is synthesized by a PCR forward primer (SEQ ID No: 15) and a PCR reverse primer(SEQ ID No: 16).

<400> SEQUENCE: 9
ctcaaaaaag acgaactgag agatgaactg aaagacgaac tgtaatga 48

<210> SEQ ID NO 10
<211> LENGTH: 14
<212> TYPE: PRT
<213> ORGANISM: Escherichia coli

<400> SEQUENCE: 10

Leu Lys Lys Asp Glu Leu Arg Asp Glu Leu Lys Asp Glu Leu
1 5 10

<210> SEQ ID NO 11
<211> LENGTH: 1965
<212> TYPE: DNA
<213> ORGANISM: Artificial Sequence
<220> FEATURE:
<223> OTHER INFORMATION: Infectious Pancreatic Necrosis Virus (IPNV) and Pseudomonas aeruginosa

<400> SEQUENCE: 11
ggatccgccg aagaagcttt cgacctctgg aacgaatgcg ccaaagcctg cgtgctcgac 60
ctcaaggacg gcgtgcgttc cagccgcatg agcgtcgacc cggccatcgc cgacaccaac 120
ggccagggcg tgctgcacta ctccatggtc ctggagggcg gcaacgacgc gctcaagctg 180
gccatcgaca acgccctcag catcaccagc gacggcctga ccatccgcct cgaaggcggc 240
gtcgagccga acaagccggt gcgctacagc tacacgcgcc aggcgcgcgg cagttggtcg 300
ctgaactggc tggtaccgat cggccacgag aagccctcga acatcaaggt gttcatccac 360
gaactgaacg ccggcaacca gctcagccac atgtcgccga tctacaccac cgagatgggc 420
gacgagttgc tagcgaagct ggcgcgcgat gccaccttct tcgtcagggc gcacgagagc 480
aacgagatgc agccgacgct cgccatcagc catgccgggg tcagcgtggt catggcccag 540
acccagccgc gccgggaaaa gcgctggagc gaatgggcca gcggcaaggt gttgtgcctg 600
ctcgacccgc tggacggggt ctacaactac ctcgcccagc aacgctgcaa cctcgacgat 660
acctgggaag gcaagatcta ccgggtgctc gccggcaacc cggcgaagca tgacctggac 720
atcaaaccca cggtcatcag tcatcgcctg cactttcccg agggcggcag cctggccgcg 780
ctgaccgcgc accaggcttg ccacctgccg ctggagactt tcacccgtca tcgccagccg 840
cgcggctggg aacaactgga gcagtgcggc tatccggtgc agcggctggt cgccctctac 900
ctggcggcgc ggctgtcgtg gaaccaggtc gaccaggtga tccgcaacgc cctggccagc 960
cccggcagcg gcggcgacct aggcgaagcg atccgcgagc agccggagca ggcccgtctg 1020
gccctgaccc tggccgccgc cgagagcgag cgcttcatcc ggcagggcac cggcaacgac 1080
gaggccggcg cggccaacgc cgacgtggtg agcctgacct gcgaattccc atacgtccgc 1140
ctagaggacg agacacccca gggtctccag tcaatgaacg gggccaagat gaggtgcaca 1200
gctgcaattg caccgcggag gtacgagatc gacctcccat cccaacgcct acccccgtt 1260

```
actgcgacag gagccctcac cactctctac gagggaaacg ccgacatcgt caactccacg    1320
acagtgacgg gagacataaa cttcagtctg acagaacaac ccgcagtcga gaccaagttc    1380
gacttccagc tggacttcat gggccttgac aacgacgtcc cagttgtcac agtggtcagc    1440
tccgtgctgg ccacaaatga caactacaga ggagtctcag ccaagatgac ccagtccatc    1500
ccgaccgaga acatcacaaa gccgatcacc agggtcaagc tgtcatacaa gatcaaccag    1560
cagacggcaa tcggcaacgt cgccaccctg ggcacaatgg gtccagcatc cgtctccttc    1620
tcatcaggga acggaaatgt ccccggcgtg ctcagaccaa tcacactggt ggcctatgag    1680
aagatgacac cgctgtccat cctgaccgta gctggagtgt ccaactacga gctgatccca    1740
aacccagaac tcctaaagaa catggtgaca cgctatggca agtacgaccc cgaaggtctc    1800
aactatgcca agatgatcct gtcccacagg gaagagctgg acatcaggac agtgtggagg    1860
acagaggagt acaaggagag gaccagagtc ttcaacgaaa tcacgaagct tctcaaaaaa    1920
gacgaactga gagatgaact gaaagacgaa ctgtaatgac tcgag                     1965
```

<210> SEQ ID NO 12
<211> LENGTH: 651
<212> TYPE: PRT
<213> ORGANISM: Artificial Sequence
<220> FEATURE:
<223> OTHER INFORMATION: Infectious Pancreatic Necrosis Virus (IPNV) and
      Pseudomonas aeruginosa

<400> SEQUENCE: 12

```
Gly Ser Ala Glu Glu Ala Phe Asp Leu Trp Asn Glu Cys Ala Lys Ala
1               5                   10                  15

Cys Val Leu Asp Leu Lys Asp Gly Val Arg Ser Ser Arg Met Ser Val
            20                  25                  30

Asp Pro Ala Ile Ala Asp Thr Asn Gly Gln Gly Val Leu His Tyr Ser
        35                  40                  45

Met Val Leu Glu Gly Gly Asn Asp Ala Leu Lys Leu Ala Ile Asp Asn
    50                  55                  60

Ala Leu Ser Ile Thr Ser Asp Gly Leu Thr Ile Arg Leu Glu Gly Gly
65                  70                  75                  80

Val Glu Pro Asn Lys Pro Val Arg Tyr Ser Tyr Thr Arg Gln Ala Arg
                85                  90                  95

Gly Ser Trp Ser Leu Asn Trp Leu Val Pro Ile Gly His Glu Lys Pro
            100                 105                 110

Ser Asn Ile Lys Val Phe Ile His Glu Leu Asn Ala Gly Asn Gln Leu
        115                 120                 125

Ser His Met Ser Pro Ile Tyr Thr Thr Glu Met Gly Asp Glu Leu Leu
    130                 135                 140

Ala Lys Leu Ala Arg Asp Ala Thr Phe Phe Val Arg Ala His Glu Ser
145                 150                 155                 160

Asn Glu Met Gln Pro Thr Leu Ala Ile Ser His Ala Gly Val Ser Val
                165                 170                 175

Val Met Ala Gln Thr Gln Pro Arg Arg Glu Lys Arg Trp Ser Glu Trp
            180                 185                 190

Ala Ser Gly Lys Val Leu Cys Leu Leu Asp Pro Leu Asp Gly Val Tyr
        195                 200                 205

Asn Tyr Leu Ala Gln Gln Arg Cys Asn Leu Asp Asp Thr Trp Glu Gly
    210                 215                 220

Lys Ile Tyr Arg Val Leu Ala Gly Asn Pro Ala Lys His Asp Leu Asp
225                 230                 235                 240
```

-continued

```
Ile Lys Pro Thr Val Ile Ser His Arg Leu His Phe Pro Glu Gly Gly
            245                 250                 255

Ser Leu Ala Ala Leu Thr Ala His Gln Ala Cys His Leu Pro Leu Glu
        260                 265                 270

Thr Phe Thr Arg His Arg Gln Pro Arg Gly Trp Glu Gln Leu Glu Gln
    275                 280                 285

Cys Gly Tyr Pro Val Gln Arg Leu Val Ala Leu Tyr Leu Ala Ala Arg
290                 295                 300

Leu Ser Trp Asn Gln Val Asp Gln Val Ile Arg Asn Ala Leu Ala Ser
305                 310                 315                 320

Pro Gly Ser Gly Gly Asp Leu Gly Glu Ala Ile Arg Glu Gln Pro Glu
                325                 330                 335

Gln Ala Arg Leu Ala Leu Thr Leu Ala Ala Glu Ser Glu Arg Phe
            340                 345                 350

Ile Arg Gln Gly Thr Gly Asn Asp Glu Ala Gly Ala Ala Asn Ala Asp
                355                 360                 365

Val Val Ser Leu Thr Cys Glu Phe Pro Tyr Val Arg Leu Glu Asp Glu
        370                 375                 380

Thr Pro Gln Gly Leu Gln Ser Met Asn Gly Ala Lys Met Arg Cys Thr
385                 390                 395                 400

Ala Ala Ile Ala Pro Arg Arg Tyr Glu Ile Asp Leu Pro Ser Gln Arg
                405                 410                 415

Leu Pro Pro Val Thr Ala Thr Gly Ala Leu Thr Thr Leu Tyr Glu Gly
            420                 425                 430

Asn Ala Asp Ile Val Asn Ser Thr Thr Val Thr Gly Asp Ile Asn Phe
        435                 440                 445

Ser Leu Thr Glu Gln Pro Ala Val Glu Thr Lys Phe Asp Phe Gln Leu
    450                 455                 460

Asp Phe Met Gly Leu Asp Asn Asp Val Pro Val Thr Val Val Ser
465                 470                 475                 480

Ser Val Leu Ala Thr Asn Asp Asn Tyr Arg Gly Val Ser Ala Lys Met
                485                 490                 495

Thr Gln Ser Ile Pro Thr Glu Asn Ile Thr Lys Pro Ile Thr Arg Val
            500                 505                 510

Lys Leu Ser Tyr Lys Ile Asn Gln Gln Thr Ala Ile Gly Asn Val Ala
        515                 520                 525

Thr Leu Gly Thr Met Gly Pro Ala Ser Val Ser Phe Ser Ser Gly Asn
    530                 535                 540

Gly Asn Val Pro Gly Val Leu Arg Pro Ile Thr Leu Val Ala Tyr Glu
545                 550                 555                 560

Lys Met Thr Pro Leu Ser Ile Leu Thr Val Ala Gly Val Ser Asn Tyr
                565                 570                 575

Glu Leu Ile Pro Asn Pro Glu Leu Leu Lys Asn Met Val Thr Arg Tyr
            580                 585                 590

Gly Lys Tyr Asp Pro Glu Gly Leu Asn Tyr Ala Lys Met Ile Leu Ser
        595                 600                 605

His Arg Glu Glu Leu Asp Ile Arg Thr Val Trp Arg Thr Glu Glu Tyr
    610                 615                 620

Lys Glu Arg Thr Arg Val Phe Asn Glu Ile Thr Lys Leu Leu Lys Lys
625                 630                 635                 640

Asp Glu Leu Arg Asp Glu Leu Lys Asp Glu Leu
                645                 650
```

<210> SEQ ID NO 13

<211> LENGTH: 1965
<212> TYPE: DNA
<213> ORGANISM: Artificial Sequence
<220> FEATURE:
<223> OTHER INFORMATION: Infectious Pancreatic Necrosis Virus (IPNV) and Pseudomonas aeruginosa

<400> SEQUENCE: 13

```
ggatccgccg aagaagcttt cgacctctgg aacgaatgcg ccaaagcctg cgtgctcgac      60
ctcaaggacg gcgtgcgttc cagccgcatg agcgtcgacc cggccatcgc cgacaccaac     120
ggccagggcg tgctgcacta ctccatggtc ctggagggcg caacgacgc gctcaagctg      180
gccatcgaca acgccctcag catcaccagc gacggcctga ccatccgcct cgaaggcggc     240
gtcgagccga caagccggt gcgctacagc tacacgcgcc aggcgcgcgg cagttggtcg      300
ctgaactggc tggtaccgat cggccacgag aagccctcga acatcaaggt gttcatccac     360
gaactgaacg ccggcaacca gctcagccac atgtcgccga tctacaccac cgagatgggc     420
gacgagttgc tagcgaagct ggcgcgcgat gccaccttct cgtcagggc gcacgagagc      480
aacgagatgc agccgacgct cgccatcagc catgccgggg tcagcgtggt catggcccag     540
acccagccgc gccgggaaaa cgctggagc gaatgggcca cggcaaggt gttgtgcctg       600
ctcgacccgc tggacggggt ctacaactac ctcgcccagc aacgctgcaa cctcgacgat     660
acctgggaag gcaagatcta ccgggtgctc gccggcaacc cggcgaagca tgacctggac     720
atcaaaccca cggtcatcag tcatcgcctg cactttcccg agggcggcag cctggccgcg     780
ctgaccgcgc accaggcttg ccacctgccg ctggagactt tcacccgtca tcgccagccg     840
cgcggctggg aacaactgga gcagtgcggc tatccggtgc agcggctggt cgccctctac     900
ctggcggcgc ggctgtcgtg gaaccaggtc gaccaggtga tccgcaacgc cctggccagc     960
cccggcagcg gcggcgacct aggcgaagcg atccgcgagc agccggagca ggcccgtctg    1020
gccctgaccc tggccgccgc cgagagcgag cgcttcatcc ggcagggcac cggcaacgac    1080
gaggccggcg cggccaacgc cgacgtggtg agcctgacct gcgaattccc atacgtccgc    1140
ctagaggacg agacacccca gggtctccag tcaatgaacg gggccaagat gaggtgcaca    1200
gctgcaattg caccgcggag gtacgagatc gacctcccat cccaacgcct acccccgtt    1260
cctgcgacag gaaccctcac cactctctac gagggaaacg ccgacatcgt caactccaca    1320
acagtgacgg gagacataaa cttcagtctg gcagaacaac ccgcaaacga gaccaagttc    1380
gacttccagc tggacttcat gggccttgac aacgacgtcc cagttgtcac agtggtcagc    1440
tccgtgctgg ccacagacga caactacaga ggagtctcag ccaagatgac ccagtccatc    1500
ccaaccgaga acatcacaaa gccgatcacc agggtcaagc tgtcatacaa gatcaaccag    1560
cagacagaaa tcggcaactt cgccaccctg ggcacaatgg gtccagcatc cgtctccttc    1620
tcatcaggga acgaaatgt ccccggcgtg ctcagaccaa tcacactggt ggcctatgag     1680
aagatgacac cgctgtccat cctgaccgta gctggagtgt ccaactacga gctgatccca    1740
aacccagaac tcctcaagaa catggtgaca cgctatggca agtacgaccc cgaaggtctc    1800
aactatgcca agatgatcct gtcccacagg gaggagctgg acatcaggac agtgtggagg    1860
acagaggagt acaaggagag gaccagagtc ttcaacgaaa tcacgaagct tctcaaaaaa    1920
gacgaactga gagatgaact gaaagacgaa ctgtaatgac tcgag                    1965
```

<210> SEQ ID NO 14
<211> LENGTH: 651
<212> TYPE: PRT
<213> ORGANISM: Artificial Sequence

```
<220> FEATURE:
<223> OTHER INFORMATION: Infectious Pancreatic Necrosis Virus (IPNV) and
      Pseudomonas aeruginosa

<400> SEQUENCE:

```
Ala Ala Ile Ala Pro Arg Arg Tyr Glu Ile Asp Leu Pro Ser Gln Arg
            405                 410                 415

Leu Pro Pro Val Pro Ala Thr Gly Thr Leu Thr Thr Leu Tyr Glu Gly
        420                 425                 430

Asn Ala Asp Ile Val Asn Ser Thr Thr Val Thr Gly Asp Ile Asn Phe
            435                 440                 445

Ser Leu Ala Glu Gln Pro Ala Asn Glu Thr Lys Phe Asp Phe Gln Leu
    450                 455                 460

Asp Phe Met Gly Leu Asp Asn Asp Val Pro Val Thr Val Val Ser
465                 470                 475                 480

Ser Val Leu Ala Thr Asn Asp Asn Tyr Arg Gly Val Ser Ala Lys Met
                485                 490                 495

Thr Gln Ser Ile Pro Thr Glu Asn Ile Thr Lys Pro Ile Thr Arg Val
            500                 505                 510

Lys Leu Ser Tyr Lys Ile Asn Gln Gln Thr Ala Ile Gly Asn Val Ala
        515                 520                 525

Thr Leu Gly Thr Met Gly Pro Ala Ser Val Ser Phe Ser Ser Gly Asn
    530                 535                 540

Gly Asn Val Pro Gly Val Leu Arg Pro Ile Thr Leu Val Ala Tyr Glu
545                 550                 555                 560

Lys Met Thr Pro Leu Ser Ile Leu Thr Val Ala Gly Val Ser Asn Tyr
                565                 570                 575

Glu Leu Ile Pro Asn Pro Glu Leu Leu Lys Asn Met Val Thr Arg Tyr
            580                 585                 590

Gly Lys Tyr Asp Pro Glu Gly Leu Asn Tyr Ala Lys Met Ile Leu Ser
        595                 600                 605

His Arg Glu Glu Leu Asp Ile Arg Thr Val Trp Arg Thr Glu Tyr
    610                 615                 620

Lys Glu Arg Thr Arg Val Phe Asn Glu Ile Thr Lys Leu Leu Lys Lys
625                 630                 635                 640

Asp Glu Leu Arg Asp Glu Leu Lys Asp Glu Leu
                645                 650

<210> SEQ ID NO 15
<211> LENGTH: 44
<212> TYPE: DNA
<213> ORGANISM: artificial sequence
<220> FEATURE:
<223> OTHER INFORMATION: A forward primer for amplifying DNA sequence
      encoding KDEL signal peptide

<400> SEQUENCE: 15
cccaagcttc tcaaaaaaga cgaactgaga gatgaactga aaga                44

<210> SEQ ID NO 16
<211> LENGTH: 37
<212> TYPE: DNA
<213> ORGANISM: artificial sequence
<220> FEATURE:
<223> OTHER INFORMATION: A reverse primer for amplifying DNA sequence
      encoding KDEL signal peptide

<400> SEQUENCE: 16
gtgctcgagt cattacagtt cgtctttcag ttcatct                       37

<210> SEQ ID NO 17
<211> LENGTH: 29
<212> TYPE: DNA
<213> ORGANISM: artificial sequence
```

```
<220> FEATURE:
<223> OTHER INFORMATION: A forward primer for amplifying DNA sequence
      encoding amino acid 173 to 431 of viral protein VP2 of IPNV

<400> SEQUENCE: 17
cggaattccc atacgtccgc ctagaggac                                      29

<210> SEQ ID NO 18
<211> LENGTH: 26
<212> TYPE: DNA
<213> ORGANISM: artificial sequence
<220> FEATURE:
<223> OTHER INFORMATION: A reverse primer for amplifying DNA sequence
      encoding amino acid 173 to 431 of viral protein VP2 of IPNV

<400> SEQUENCE: 18
cccaagcttc gtgatttcgt tgaaga                                         26

<210> SEQ ID NO 19
<211> LENGTH: 41
<212> TYPE: DNA
<213> ORGANISM: artificial sequence
<220> FEATURE:
<223> OTHER INFORMATION: A forward primer for amplifying DNA sequence
      encoding the receptor binding motif and translocation domain of
      exotoxin A protein (PE protein)

<400> SEQUENCE: 19
cgggatccgc cgaagaagct ttcgacctct ggaacgaatg c                        41

<210> SEQ ID NO 20
<211> LENGTH: 26
<212> TYPE: DNA
<213> ORGANISM: artificial sequence
<220> FEATURE:
<223> OTHER INFORMATION: A reverse primer for amplifying DNA sequence
      encoding the receptor binding motif and translocation domain of
      exotoxin A protein (PE protein)

<400> SEQUENCE: 20
cggaattcgc aggtcaggct caccac                                         26

<210> SEQ ID NO 21
<211> LENGTH: 1527
<212> TYPE: DNA
<213> ORGANISM: Infectious Hematopoietic Necrosis Virus (HNV)
<300> PUBLICATION INFORMATION:
<308> DATABASE ACCESSION NUMBER: Genbank/NC_001652
<309> DATABASE ENTRY DATE: 2006-03-30
<313> RELEVANT RESIDUES IN SEQ ID NO: (2999)...(4525)

<400> SEQUENCE: 21
atggacacca tgatcaccac tccgctcatt ctcattctga tcacctgcgg agcaaacagc     60
caaaccgtca aacccgacac cgcaagcgaa tcagaccaaa ccacctggtc aaacccgctc    120
ttcacctatc ccgagggatg cactctggac aagctctcta aggtcaatgc ctctcaactg    180
agatgcccaa ggatcttcga cgatgagaac aggggggctaa ttgcctatcc cacatccatc    240
cggtccctgt cagtcggaaa cgacctcggg gacattcaca cccaagggaa ccacatccac    300
aaagtcctgt accgcacaat ctgctcaaca ggttcttcg ggggtcagac gatagagaag    360
gcgcttgtaa aaatgaaact ctctacgaaa gaagcagggg cgtatgacac cacaaccgca    420
gccgctctgt acttcccagc tccccgatgc caatggtaca ccgacaacgt acaaaacgat    480
ctcatcttct actacacaac acaaaagagt gttcttagag atccctacac cagagacttt    540
ctggactcag attttattgg aggaaaatgt gtccaaatcac cctgccagac tcattggtcc    600
```

| | |
|---|---:|
| aacgtagttt ggatgggtga tgcagggata ccagcctgtg attccagcca agagataaaa | 660 |
| gctcacctct ttgttgataa aatctccaat cgagtcgtga aggcaacgag ctacggacac | 720 |
| cacccctggg gactgcatca ggcctgtatg attgaattct gtgggcaaca gtggatacgg | 780 |
| acagatctcg gtgacctaat atctgtcgta tacaattctg gatcagaaat cctctcgttc | 840 |
| ccgaagtgtg aagacaagac cgtgggaatg aggggaaact tggatgactt tgcctatcta | 900 |
| gacgatctgg tgaaggcctc tgagagcaga gaggaatgtc ttgaggcgca cgccgagata | 960 |
| atatcaacaa acagtgtgac tccatacctc ctatccaaat tccgatctcc acatcccgga | 1020 |
| ataaatgacg tctacgctat gcacaaaggc tccatctatc acgggatgtg catgacggtc | 1080 |
| gctgtggacg aggtatccaa ggacaggaca acgtacaggg cccatcgcgc taccagcttc | 1140 |
| acgaaatggg aacgaccctt tggggatgag tgggagggct tcacggatt gcacggaaac | 1200 |
| aacaccacca ttattccaga cctggagaaa tacgtcgccc agtacaagat gagcatgatg | 1260 |
| gaaccgatga gcatcaaatc cgtaccccat ccaagcatcc tggccctcta caatgagaca | 1320 |
| gacgtgtcag ggatctccat caggaaactg gactcattcg accttcaatc actccactgg | 1380 |
| agtttctggc ccacaatctc cgcactgggt ggaattccct ttgttctcct ccttgctgtt | 1440 |
| gccgcgtgct gctgctggtc agggagacct cccactccct ccgtgccgca gagtatcccc | 1500 |
| atgtatcacc tggcaaaccg gtcctaa | 1527 |

<210> SEQ ID NO 22
<211> LENGTH: 508
<212> TYPE: PRT
<213> ORGANISM: Infectious Hematopoietic Necrosis Virus (IHNV)
<300> PUBLICATION INFORMATION:
<308> DATABASE ACCESSION NUMBER: Genbank/NP_042679
<309> DATABASE ENTRY DATE: 2006-03-30

<400> SEQUENCE: 22

Met Asp Thr Met Ile Thr Thr Pro Leu Ile Leu Ile Leu Ile Thr Cys
1               5                   10                  15

Gly Ala Asn Ser Gln Thr Val Lys Pro Asp Thr Ala Ser Glu Ser Asp
            20                  25                  30

Gln Pro Thr Trp Ser Asn Pro Leu Phe Thr Tyr Pro Glu Gly Cys Thr
        35                  40                  45

Leu Asp Lys Leu Ser Lys Val Asn Ala Ser Gln Leu Arg Cys Pro Arg
    50                  55                  60

Ile Phe Asp Asp Glu Asn Arg Gly Leu Ile Ala Tyr Pro Thr Ser Ile
65                  70                  75                  80

Arg Ser Leu Ser Val Gly Asn Asp Leu Gly Asp Ile His Thr Gln Gly
                85                  90                  95

Asn His Ile His Lys Val Leu Tyr Arg Thr Ile Cys Ser Thr Gly Phe
            100                 105                 110

Phe Gly Gly Gln Thr Ile Glu Lys Ala Leu Val Lys Met Lys Leu Ser
        115                 120                 125

Thr Lys Glu Ala Gly Ala Tyr Asp Thr Thr Thr Ala Ala Ala Leu Tyr
    130                 135                 140

Phe Pro Ala Pro Arg Cys Gln Trp Tyr Thr Asp Asn Val Gln Asn Asp
145                 150                 155                 160

Leu Ile Phe Tyr Tyr Thr Thr Gln Lys Ser Val Leu Arg Asp Pro Tyr
                165                 170                 175

Thr Arg Asp Phe Leu Asp Ser Asp Phe Ile Gly Gly Lys Cys Thr Lys
            180                 185                 190

```
Ser Pro Cys Gln Thr His Trp Ser Asn Val Val Trp Met Gly Asp Ala
        195                 200                 205

Gly Ile Pro Ala Cys Asp Ser Ser Gln Glu Ile Lys Ala His Leu Phe
    210                 215                 220

Val Asp Lys Ile Ser Asn Arg Val Val Lys Ala Thr Ser Tyr Gly His
225                 230                 235                 240

His Pro Trp Gly Leu His Gln Ala Cys Met Ile Glu Phe Cys Gly Gln
                245                 250                 255

Gln Trp Ile Arg Thr Asp Leu Gly Asp Leu Ile Ser Val Val Tyr Asn
            260                 265                 270

Ser Gly Ser Glu Ile Leu Ser Phe Pro Lys Cys Glu Asp Lys Thr Val
        275                 280                 285

Gly Met Arg Gly Asn Leu Asp Asp Phe Ala Tyr Leu Asp Asp Leu Val
    290                 295                 300

Lys Ala Ser Glu Ser Arg Glu Glu Cys Leu Glu Ala His Ala Glu Ile
305                 310                 315                 320

Ile Ser Thr Asn Ser Val Thr Pro Tyr Leu Leu Ser Lys Phe Arg Ser
                325                 330                 335

Pro His Pro Gly Ile Asn Asp Val Tyr Ala Met His Lys Gly Ser Ile
            340                 345                 350

Tyr His Gly Met Cys Met Thr Val Ala Val Asp Glu Val Ser Lys Asp
        355                 360                 365

Arg Thr Thr Tyr Arg Ala His Arg Ala Thr Ser Phe Thr Lys Trp Glu
    370                 375                 380

Arg Pro Phe Gly Asp Glu Trp Glu Gly Phe His Gly Leu His Gly Asn
385                 390                 395                 400

Asn Thr Thr Ile Ile Pro Asp Leu Glu Lys Tyr Val Ala Gln Tyr Lys
                405                 410                 415

Met Ser Met Met Glu Pro Met Ser Ile Lys Ser Val Pro His Pro Ser
            420                 425                 430

Ile Leu Ala Leu Tyr Asn Glu Thr Asp Val Ser Gly Ile Ser Ile Arg
        435                 440                 445

Lys Leu Asp Ser Phe Asp Leu Gln Ser Leu His Trp Ser Phe Trp Pro
    450                 455                 460

Thr Ile Ser Ala Leu Gly Gly Ile Pro Phe Val Leu Leu Ala Val
465                 470                 475                 480

Ala Ala Cys Cys Cys Trp Ser Gly Arg Pro Pro Thr Pro Ser Val Pro
                485                 490                 495

Gln Ser Ile Pro Met Tyr His Leu Ala Asn Arg Ser
            500                 505

<210> SEQ ID NO 23
<211> LENGTH: 1176
<212> TYPE: DNA
<213> ORGANISM: Infectious Hematopoietic Necrosis Virus (IHNV)
<300> PUBLICATION INFORMATION:
<308> DATABASE ACCESSION NUMBER: Genbank/NC_001652
<309> DATABASE ENTRY DATE: 2006-03-30
<313> RELEVANT RESIDUES IN SEQ ID NO: (175)...(1350)

<400> SEQUENCE: 23
atgacaagcg cactcagaga gacgttcact ggactcagag acatcaaggg gggagtcctc      60
gaggatccag agacggagta tcgtcccagt acgataaccc tccctctatt tttctccaag     120
acagacttag acctagagat gatcaagcgg cggtgagtc aagtcggagg agagggaacg     180
agaaaggcat tgagcctcct gtgcgcgttc gtcattgcag agacggtccc atcggaggca     240
```

-continued

```
ggtacggtcg ccgaacttct ggaagccctg ggtttcgtgc tggagtcttt ggacactggg    300
gcaccaccag acgctacctt cgcagatccc aacaacaagc ttgcagaaac gatcgtaaag    360
gaaaatgtcc ttgaggttgt gaccggcctc ctcttcacct gcgccctact gactaagtat    420
gatgtggaca gatgccac atactgccaa acaagctcg agcgtcttgc aaccagccaa       480
gggattggcg agttggttaa cttcaacgcc aacaggggag tcctggccaa gatcggggcg    540
gtgcttagac ccggacagaa gctcaccaag gctatctatg gatcattct catcaacctg     600
tccgacccag ccatcgctgc cagagccaag gcactgtgcg ccatgagact gagcgggaca    660
ggaatgacaa tggtggggct gttcaaccaa gccgcaaaga acctgggcgc ccttccagcc    720
gaccttttag aggatctgtg catgaagtca gtggtggagt ccgccagacg cattgtcaga    780
ctgatgagga tcgtagcaga ggccccaggg gtagcagcaa agtacggtgt catgatgagc    840
aggatgctcg gggaggggta cttcaaggcc tacgggatca cgagaacgc caggatcacc     900
tgcattctca tgaacatcaa cgataggtat gacgatggga cctcgagagg actgacaggg    960
ataaaggtct ccgacccttt caggaagctg gcgagggaga tcgctcgtct ccttgtcctc   1020
aagtacgatg gcgatggctc aaccggagag ggggcgtcag agctgatccg ccgggcggag   1080
atggcatctc ggggaccaga catgggtgag gaggaggagg aggacgagga ggacgacgac   1140
tccagtgagc aggagactc cgactcattc cactga                              1176
```

<210> SEQ ID NO 24
<211> LENGTH: 391
<212> TYPE: PRT
<213> ORGANISM: Infectious Hematopoietic Necrosis Virus (IHNV)
<300> PUBLICATION INFORMATION:
<308> DATABASE ACCESSION NUMBER: Genbank/NP_042676
<309> DATABASE ENTRY DATE: 2006-03-30

<400> SEQUENCE: 24

```
Met Thr Ser Ala Leu Arg Glu Thr Phe Thr Gly Leu Arg Asp Ile Lys
1               5                   10                  15

Gly Gly Val Leu Glu Asp Pro Glu Thr Glu Tyr Arg Pro Ser Thr Ile
            20                  25                  30

Thr Leu Pro Leu Phe Phe Ser Lys Thr Asp Leu Asp Leu Glu Met Ile
        35                  40                  45

Lys Arg Ala Val Ser Gln Val Gly Gly Glu Gly Thr Arg Lys Ala Leu
    50                  55                  60

Ser Leu Leu Cys Ala Phe Val Ile Ala Glu Thr Val Pro Ser Glu Ala
65                  70                  75                  80

Gly Thr Val Ala Glu Leu Leu Glu Ala Leu Gly Phe Val Leu Glu Ser
                85                  90                  95

Leu Asp Thr Gly Ala Pro Pro Asp Ala Thr Phe Ala Asp Pro Asn Asn
            100                 105                 110

Lys Leu Ala Glu Thr Ile Val Lys Glu Asn Val Leu Glu Val Val Thr
        115                 120                 125

Gly Leu Leu Phe Thr Cys Ala Leu Leu Thr Lys Tyr Asp Val Asp Lys
    130                 135                 140

Met Ala Thr Tyr Cys Gln Asn Lys Leu Glu Arg Leu Ala Thr Ser Gln
145                 150                 155                 160

Gly Ile Gly Glu Leu Val Asn Phe Asn Ala Asn Arg Gly Val Leu Ala
                165                 170                 175

Lys Ile Gly Ala Val Leu Arg Pro Gly Gln Lys Leu Thr Lys Ala Ile
            180                 185                 190

Tyr Gly Ile Ile Leu Ile Asn Leu Ser Asp Pro Ala Ile Ala Ala Arg
```

```
                195                 200                 205
Ala Lys Ala Leu Cys Ala Met Arg Leu Ser Gly Thr Gly Met Thr Met
210                 215                 220

Val Gly Leu Phe Asn Gln Ala Ala Lys Asn Leu Gly Ala Leu Pro Ala
225                 230                 235                 240

Asp Leu Leu Glu Asp Leu Cys Met Lys Ser Val Val Glu Ser Ala Arg
                245                 250                 255

Arg Ile Val Arg Leu Met Arg Ile Val Ala Glu Ala Pro Gly Val Ala
            260                 265                 270

Ala Lys Tyr Gly Val Met Met Ser Arg Met Leu Gly Glu Gly Tyr Phe
        275                 280                 285

Lys Ala Tyr Gly Ile Asn Glu Asn Ala Arg Ile Thr Cys Ile Leu Met
290                 295                 300

Asn Ile Asn Asp Arg Tyr Asp Asp Gly Thr Ser Arg Gly Leu Thr Gly
305                 310                 315                 320

Ile Lys Val Ser Asp Pro Phe Arg Lys Leu Ala Arg Glu Ile Ala Arg
                325                 330                 335

Leu Leu Val Leu Lys Tyr Asp Gly Asp Gly Ser Thr Gly Glu Gly Ala
            340                 345                 350

Ser Glu Leu Ile Arg Arg Ala Glu Met Ala Ser Arg Gly Pro Asp Met
        355                 360                 365

Gly Glu Glu Glu Glu Asp Glu Glu Asp Asp Ser Ser Glu Pro
370                 375                 380

Gly Asp Ser Asp Ser Phe His
385                 390

<210> SEQ ID NO 25
<211> LENGTH: 1023
<212> TYPE: DNA
<213> ORGANISM: Nervous Necrosis Virus (NNV)
<300> PUBLICATION INFORMATION:
<308> DATABASE ACCESSION NUMBER: Genbank/NC_003449
<309> DATABASE ENTRY DATE: 2006-08-11
<313> RELEVANT RESIDUES IN SEQ ID NO: (28)...(1050)

<400> SEQUENCE: 25
atggtacgca aaggtgataa gaaattggca aaaccccga ccacaaaggc cgccaattct      60
caaccacgtc gacgtgcaac acagcgccgt cgcagtggta gggctgatgc acccttagct    120
aaggcatcga ctatcacggg atttggacgt gcgaccaatg atgtccatat ctcgggaatg    180
tcacggatcg ctcaagcagt tgttccagcc gggacaggaa cagatggaaa gattgtcgtc    240
gattccacaa tcgttccaga actcctgcca cggcttggac acgctgctcg aatcttccag    300
cgatacgctt tgaaacact ggagttcgaa attcagccaa tgtgccccgc aaacacgggc      360
ggtggttacg ttgctggctt cctgcctgat ccaactgaca cgaccacac cttcgatgcg      420 ctccaagcaa ctcgtggtgc agtcgtcgcc aaatggtggg aaagtcgaac agtccggccc    480
cagtatactc gaacgcttct ctggacctca accgggaagg agcagcgatt gacatcacct    540
ggccggctgg tactcctgtg tgttggcagc aacactgatt tgtcaacgt gtcagtcatg      600 tgtcgctgga gcgttcgcct tagtgtcccg tcccttgaga cacctgagga caccaccgct    660
ccaattacta cccaggcgcc actccacaac gattccatta caacggtta cactggattt      720 cgttccattc tcttgggcgc gacccaactc gacctcgctc ctgcaaacgc tgtctttgtc    780
actgacaaac cgttgcccat tgattacaat cttggagtgg cgacgtcga ccgggccgtg      840 tactggcacc tgcggaagaa agctggagac actcaggtac ctgctgggta ctttgactgg    900
```

```
ggactgtggg atgactttaa caagacattc acagttgggg caccctacta ctccgaccag    960
caaccacggc aaatcttgct gccggctggc acgctcttca cccgtgttga ctcggaaaac   1020
taa                                                                 1023
```

<210> SEQ ID NO 26
<211> LENGTH: 340
<212> TYPE: PRT
<213> ORGANISM: Nervous Necrosis Virus (NNV)
<300> PUBLICATION INFORMATION:
<308> DATABASE ACCESSION NUMBER: Genbank/NP_599429
<309> DATABASE ENTRY DATE: 2006-08-11

<400> SEQUENCE: 26

```
Met Val Arg Lys Gly Asp Lys Lys Leu Ala Lys Pro Pro Thr Thr Lys
1               5                   10                  15

Ala Ala Asn Ser Gln Pro Arg Arg Ala Thr Gln Arg Arg Ser
            20                  25                  30

Gly Arg Ala Asp Ala Pro Leu Ala Lys Ala Ser Thr Ile Thr Gly Phe
        35                  40                  45

Gly Arg Ala Thr Asn Asp Val His Ile Ser Gly Met Ser Arg Ile Ala
    50                  55                  60

Gln Ala Val Val Pro Ala Gly Thr Gly Thr Asp Gly Lys Ile Val Val
65                  70                  75                  80

Asp Ser Thr Ile Val Pro Glu Leu Leu Pro Arg Leu Gly His Ala Ala
                85                  90                  95

Arg Ile Phe Gln Arg Tyr Ala Val Glu Thr Leu Glu Phe Glu Ile Gln
            100                 105                 110

Pro Met Cys Pro Ala Asn Thr Gly Gly Gly Tyr Val Ala Gly Phe Leu
        115                 120                 125

Pro Asp Pro Thr Asp Asn Asp His Thr Phe Asp Ala Leu Gln Ala Thr
    130                 135                 140

Arg Gly Ala Val Val Ala Lys Trp Trp Glu Ser Arg Thr Val Arg Pro
145                 150                 155                 160

Gln Tyr Thr Arg Thr Leu Leu Trp Thr Ser Thr Gly Lys Glu Gln Arg
                165                 170                 175

Leu Thr Ser Pro Gly Arg Leu Val Leu Leu Cys Val Gly Ser Asn Thr
            180                 185                 190

Asp Val Asn Val Ser Val Met Cys Arg Trp Ser Val Arg Leu Ser
        195                 200                 205

Val Pro Ser Leu Glu Thr Pro Glu Asp Thr Thr Ala Pro Ile Thr Thr
    210                 215                 220

Gln Ala Pro Leu His Asn Asp Ser Ile Asn Asn Gly Tyr Thr Gly Phe
225                 230                 235                 240

Arg Ser Ile Leu Leu Gly Ala Thr Gln Leu Asp Leu Ala Pro Ala Asn
                245                 250                 255

Ala Val Phe Val Thr Asp Lys Pro Leu Pro Ile Asp Tyr Asn Leu Gly
            260                 265                 270

Val Gly Asp Val Asp Arg Ala Val Tyr Trp His Leu Arg Lys Lys Ala
        275                 280                 285

Gly Asp Thr Gln Val Pro Ala Gly Tyr Phe Asp Trp Gly Leu Trp Asp
    290                 295                 300

Asp Phe Asn Lys Thr Phe Thr Val Gly Ala Pro Tyr Tyr Ser Asp Gln
305                 310                 315                 320

Gln Pro Arg Gln Ile Leu Leu Pro Ala Gly Thr Leu Phe Thr Arg Val
                325                 330                 335
```

Asp Ser Glu Asn
        340

<210> SEQ ID NO 27
<211> LENGTH: 1362
<212> TYPE: DNA
<213> ORGANISM: Grouper Iridovirus (GIV)
<300> PUBLICATION INFORMATION:
<308> DATABASE ACCESSION NUMBER: Genbank/AY894343
<309> DATABASE ENTRY DATE: 2005-08-04
<313> RELEVANT RESIDUES IN SEQ ID NO: (3793)...(5154)

<400> SEQUENCE: 27

| ttacaggata gggaagcctg cagcgccgtc agcaatcttc atgatgttgt ggttgactgc | 60 |
| aataacgacc agttcaaact tttgggcgac cgtgtagccg gtgccgttgc ctccaccgcc | 120 |
| cgccgcggtg gtcttggcat tgtccgacac cttacatgac agggtgacgt tggacaggcg | 180 |
| gccgtagttg gtcgagccca tagggttgat attgcccatg tccagcgtat aacagtaggt | 240 |
| cataacacca tccatctcag gcatgctggg cgcaaagtag taggggtcga cagatgtgaa | 300 |
| gtagtctact cccatctggt ggagccgagg ggtgttctcg taaatgagcg cacctcgga | 360 |
| caggggattg gtggccagca aaggcagatt caccttgttg ttgacataca cgggactggc | 420 |
| cgcggtgtaa ttgctttgca cgttgcggtg agtgacattc ttgactgcaa gaacaaggc | 480 |
| cttcacaggg tgactgaacc tcaggtcgag atgcaccaag gaattgtcta cgggtgtgac | 540 |
| aggcacacga ggcgccacct gacactgctc aatgagcatg ctacggctag actgggccac | 600 |
| aacctcacgc tcctcacttg tcagtacagc gtaggtgccc atcacggaca cgttggtcag | 660 |
| tgcgggtgct acattgccaa tgttagccag ggtgacagtc gatatggcca tgtcggcctg | 720 |
| ggtgctctgg ctgatgagca ggtcctccca gcgccgcagc ttgaagtgga tgcgcacctc | 780 |
| attgtacggc agagacacag taggcaatgc aaggcctgtg tcacgggtaa gaacagggg | 840 |
| aatgggcaaa ttaaggtagg cggcgggcat agtctgaccg ttggtgatac cgcccaccag | 900 |
| gtcgctgcgc atgccaatca tcttgttgta gccagattgt ttgctgccag gcatcatgca | 960 |
| ggcgttccaa aagtcaagga actcgctggt cagggtctgt gccaccaggt cgttaaatga | 1020 |
| caccgacacc tcctcaacta gattgtgcat caaattatca caccagcgaa tgtagctgtt | 1080 |
| ctccttgctg gacgtgatgg aggggatctt aacacgcagc cacacattaa tgaggtagtc | 1140 |
| gccacccctt gccacagtca cactaaactc ctggccgaaa ttagcatggc cagtctgttt | 1200 |
| tgatagggtg acgggcagct tgctgtacca ggaactacgc acggtctcac gggcaaagta | 1260 |
| ggtcacggca ttgtcgccgc catacaagtg ggtctccatc gcatcaaacg cggagatgtc | 1320 |
| gatgaaccca ctggttacgt tcgcacctga gattgcagac at | 1362 |

<210> SEQ ID NO 28
<211> LENGTH: 453
<212> TYPE: PRT
<213> ORGANISM: Grouper Iridovirus (GIV)
<300> PUBLICATION INFORMATION:
<308> DATABASE ACCESSION NUMBER: Genbank/AAX82316
<309> DATABASE ENTRY DATE: 2005-08-04

<400> SEQUENCE: 28

Met Ser Ala Ile Ser Gly Ala Asn Val Thr Ser Gly Phe Ile Asp Ile
1 5 10 15

Ser Ala Phe Asp Ala Met Glu Thr His Leu Tyr Gly Gly Asp Asn Ala
20 25 30

Val Thr Tyr Phe Ala Arg Glu Thr Val Arg Ser Ser Trp Tyr Ser Lys
35 40 45

```
Leu Pro Val Thr Leu Ser Lys Gln Thr Gly His Ala Asn Phe Gly Gln
    50                  55                  60

Glu Phe Ser Val Thr Val Ala Arg Gly Gly Asp Tyr Leu Ile Asn Val
65                  70                  75                  80

Trp Leu Arg Val Lys Ile Pro Ser Ile Thr Ser Lys Glu Asn Ser
                85                  90                  95

Tyr Ile Arg Trp Cys Asp Asn Leu Met His Asn Leu Val Glu Glu Val
            100                 105                 110

Ser Val Ser Phe Asn Asp Leu Val Ala Gln Thr Leu Thr Ser Glu Phe
            115                 120                 125

Leu Asp Phe Trp Asn Ala Cys Met Met Pro Gly Ser Lys Gln Ser Gly
    130                 135                 140

Tyr Asn Lys Met Ile Gly Met Arg Ser Asp Leu Val Gly Gly Ile Thr
145                 150                 155                 160

Asn Gly Gln Thr Met Pro Ala Ala Tyr Leu Asn Leu Pro Ile Pro Leu
                165                 170                 175

Phe Phe Thr Arg Asp Thr Gly Leu Ala Leu Pro Thr Val Ser Leu Pro
            180                 185                 190

Tyr Asn Glu Val Arg Ile His Phe Lys Leu Arg Arg Trp Glu Asp Leu
            195                 200                 205

Leu Ile Ser Gln Ser Thr Gln Ala Asp Met Ala Ile Ser Thr Val Thr
    210                 215                 220

Leu Ala Asn Ile Gly Asn Val Ala Pro Ala Leu Thr Asn Val Ser Val
225                 230                 235                 240

Met Gly Thr Tyr Ala Val Leu Thr Ser Glu Glu Arg Glu Val Val Ala
                245                 250                 255

Gln Ser Ser Arg Ser Met Leu Ile Glu Gln Cys Gln Val Ala Pro Arg
            260                 265                 270

Val Pro Val Thr Pro Val Asp Asn Ser Leu Val His Leu Asp Leu Arg
            275                 280                 285

Phe Ser His Pro Val Lys Ala Leu Phe Phe Ala Val Lys Asn Val Thr
    290                 295                 300

His Arg Asn Val Gln Ser Asn Tyr Thr Ala Ala Ser Pro Val Tyr Val
305                 310                 315                 320

Asn Asn Lys Val Asn Leu Pro Leu Leu Ala Thr Asn Pro Leu Ser Glu
                325                 330                 335

Val Ser Leu Ile Tyr Glu Asn Thr Pro Arg Leu His Gln Met Gly Val
            340                 345                 350

Asp Tyr Phe Thr Ser Val Asp Pro Tyr Tyr Phe Ala Pro Ser Met Pro
        355                 360                 365

Glu Met Asp Gly Val Met Thr Tyr Cys Tyr Thr Leu Asp Met Gly Asn
    370                 375                 380

Ile Asn Pro Met Gly Ser Thr Asn Tyr Gly Arg Leu Ser Asn Val Thr
385                 390                 395                 400

Leu Ser Cys Lys Val Ser Asp Asn Ala Lys Thr Thr Ala Ala Gly Gly
                405                 410                 415

Gly Gly Asn Gly Thr Gly Tyr Thr Val Ala Gln Lys Phe Glu Leu Val
            420                 425                 430

Val Ile Ala Val Asn His Asn Ile Met Lys Ile Ala Asp Gly Ala Ala
        435                 440                 445

Gly Phe Pro Ile Leu
    450
```

<210> SEQ ID NO 29
<211> LENGTH: 1458
<212> TYPE: DNA
<213> ORGANISM: Grouper Iridovirus (GIV)
<300> PUBLICATION INFORMATION:
<308> DATABASE ACCESSION NUMBER: Genbank/AY894343
<309> DATABASE ENTRY DATE: 2005-08-04
<313> RELEVANT RESIDUES IN SEQ ID NO: (5171)...(6628)

<400> SEQUENCE: 29

| | | | | | |
|---|---|---|---|---|---|
| ttatatatga | tcggcctcgt | ttttcttctg | gaaacctgca | ctcagcaaga | ccaacagtcc | 60 |
| gaccgcggcg | atggtgcctc | ctgtgcccag | gaccacattg | gtggctgtgg | tgtcacacgg | 120 |
| catgcccgcc | accacggtcg | tgttggggtc | tctcggcgtg | aacgcagtgt | ctatgttcaa | 180 |
| ggtgccgggc | acgtcctgcc | acgtgccgta | agccttctta | atacgcacct | tgtggttgag | 240 |
| gcgagagcgc | tcgtagtaga | acatgatcca | cacatcgtag | ccatcgagcg | ccccgccgtg | 300 |
| gccccagccc | agcttctttg | cggcacccaa | aacatcgggc | ttgatgtcct | gcaccttgcc | 360 |
| cctgcgctgc | caaccgtcct | cgttcatcac | atagtacgta | ccgctttcac | tgtgcaggta | 420 |
| cgcgtcgccc | ggtttcattg | tggccgtcgt | gccagagtcc | ttggggtcag | gcttggtgtc | 480 |
| tgtggccagg | ttcagcttgt | agcgtatcat | aggcttgaca | cgacgggca | gttgcgcggg | 540 |
| catgacgtat | gcggtggcct | tgggcagcag | cacaggtgcg | ccgtccgagt | cagccttgta | 600 |
| ccgctcatag | tacaccatct | ggccctgggc | cagcttcgcc | accgcctggt | ccagggtgac | 660 |
| gtcggtgaac | ttttgcgcgc | tgtccagcga | gcccggggcg | acggcatgcg | gatacaccaa | 720 |
| gggctcagca | ccctttgcct | gacgacacat | gaacttgaaa | gcatacgccg | ccacgcctat | 780 |
| gccacccacc | aagagcacca | tgccgattac | cccacgcttg | cccaatatgg | agccggtggc | 840 |
| caggggcatg | ccgatgagca | ggcccgccag | cacggcggcc | agctgccaca | ggtccacacc | 900 |
| ctgggccttg | gcggtggcca | gctgctgaag | cttgttcacc | acatcctgca | tgctgctgct | 960 |
| gctggccgtg | gcgtcctgca | cgcactgcga | cagggccgac | acgaagatgc | gcagcacaga | 1020 |
| gtcctggatg | acgacgttgc | ccgtcacatt | gtccacagag | atcacctgtt | tggtgttgac | 1080 |
| ctcgccgctg | cacgtcagcg | tcatgttgtt | gacaatgcgg | acgtcacac | tgagaaattg | 1140 |
| ctttatgctg | tttgtggccg | aggcgtactg | accaaagttg | atgccgctca | ccacggacgc | 1200 |
| cgcctgctgt | gccatgtcgt | tgagcacctt | ctgctgagtt | tcttggttgg | ccagggcctt | 1260 |
| catggtggcc | tgaaggttca | cggtgaccgt | ctgctccatg | gtcacaccct | tgataatcac | 1320 |
| atcaccttta | acgtgagata | tattgatgat | ctgcgacgag | tctgcggtca | gcttggtgtt | 1380 |
| gttggcaatg | ttggatgtgg | cctcggccac | ggccttcagg | acagtgtcga | ccccgttgaa | 1440 |
| tgactgggca | gcacccat | | | | | 1458 |

<210> SEQ ID NO 30
<211> LENGTH: 485
<212> TYPE: PRT
<213> ORGANISM: Grouper Iridovirus (GIV)
<300> PUBLICATION INFORMATION:
<308> DATABASE ACCESSION NUMBER: Genbank/AAX82317
<309> DATABASE ENTRY DATE: 2005-08-04

<400> SEQUENCE: 30

```
Met Gly Ala Ala Gln Ser Phe Asn Gly Val Asp Thr Val Leu Lys Ala
1               5                   10                  15

Val Ala Glu Ala Thr Ser Asn Ile Ala Asn Asn Thr Lys Leu Thr Ala
            20                  25                  30

Asp Ser Ser Gln Ile Ile Asn Ile Ser His Val Lys Gly Asp Val Ile
        35                  40                  45
```

```
Ile Lys Gly Val Thr Met Glu Gln Thr Val Thr Val Asn Leu Gln Ala
 50                  55                  60

Thr Met Lys Ala Leu Ala Asn Gln Glu Thr Gln Gln Lys Val Leu Asn
 65                  70                  75                  80

Asp Met Ala Gln Gln Ala Ala Ser Val Val Ser Gly Ile Asn Phe Gly
                 85                  90                  95

Gln Tyr Ala Ser Ala Thr Asn Ser Ile Lys Gln Phe Leu Ser Val Thr
                100                 105                 110

Ser Arg Ile Val Asn Asn Met Thr Leu Thr Cys Ser Gly Glu Val Asn
            115                 120                 125

Thr Lys Gln Val Ile Ser Val Asp Asn Val Thr Gly Asn Val Val Ile
130                 135                 140

Gln Asp Ser Val Leu Arg Ile Phe Val Ser Ala Leu Ser Gln Cys Val
145                 150                 155                 160

Gln Asp Ala Thr Ala Ser Ser Ser Ser Met Gln Asp Val Val Asn Lys
                165                 170                 175

Leu Gln Gln Leu Ala Thr Ala Lys Ala Gln Gly Val Asp Leu Trp Gln
                180                 185                 190

Leu Ala Ala Val Leu Ala Gly Leu Leu Ile Gly Met Pro Leu Ala Thr
                195                 200                 205

Gly Ser Ile Leu Gly Lys Arg Gly Val Ile Gly Met Val Leu Leu Val
210                 215                 220

Gly Gly Ile Gly Val Ala Ala Tyr Ala Phe Lys Phe Met Cys Arg Gln
225                 230                 235                 240

Ala Lys Gly Ala Glu Pro Leu Val Tyr Pro His Ala Val Ala Pro Gly
                245                 250                 255

Ser Leu Asp Ser Ala Gln Lys Phe Thr Asp Val Thr Leu Asp Gln Ala
                260                 265                 270

Val Ala Lys Leu Ala Gln Gly Gln Met Val Tyr Tyr Glu Arg Tyr Lys
                275                 280                 285

Ala Asp Ser Asp Gly Ala Pro Val Leu Leu Pro Lys Ala Thr Ala Tyr
                290                 295                 300

Val Met Pro Ala Gln Leu Pro Val Val Lys Pro Met Ile Arg Tyr
305                 310                 315                 320

Lys Leu Asn Leu Ala Thr Asp Thr Lys Pro Asp Pro Lys Asp Ser Gly
                325                 330                 335

Thr Thr Ala Thr Met Lys Pro Gly Asp Ala Tyr Leu His Ser Glu Ser
                340                 345                 350

Gly Thr Tyr Tyr Val Met Asn Glu Asp Gly Trp Gln Arg Arg Gly Lys
                355                 360                 365

Val Gln Asp Ile Lys Pro Asp Val Leu Gly Ala Ala Lys Lys Leu Gly
                370                 375                 380

Trp Gly His Gly Gly Ala Leu Asp Gly Tyr Asp Val Trp Ile Met Phe
385                 390                 395                 400

Tyr Tyr Glu Arg Ser Arg Leu Asn His Lys Val Arg Ile Lys Lys Ala
                405                 410                 415

Asp Gly Thr Trp Gln Asp Val Pro Gly Thr Leu Asn Ile Asp Thr Ala
                420                 425                 430

Phe Thr Pro Arg Asp Pro Asn Thr Val Val Ala Gly Met Pro Cys
                435                 440                 445

Asp Thr Thr Ala Thr Asn Val Val Leu Gly Thr Gly Gly Thr Ile Ala
                450                 455                 460

Ala Val Gly Leu Leu Val Leu Leu Ser Ala Gly Phe Gln Lys Lys Asn
```

-continued

```
465                 470                 475                 480

Glu Ala Asp His Ile
                485

<210> SEQ ID NO 31
<211> LENGTH: 1530
<212> TYPE: DNA
<213> ORGANISM: Spring Viremia of Carp Virus (SVCV)
<300> PUBLICATION INFORMATION:
<308> DATABASE ACCESSION NUMBER: Genbank/NC_002803
<309> DATABASE ENTRY DATE: 2006-05-16
<313> RELEVANT RESIDUES IN SEQ ID NO: (3094)...(4623)

<400> SEQUENCE: 31
atgtctatca tcagctacat cgcattcctt ttgctaattg actccaactt aggaatcccc      60
atatttgttc catctggtcg aaatatatca tggcagcctg tgattcagcc atttgattat     120
caatgtccaa tccatggaaa cctacccaac acgatgggtt tgagtgccac caaattgaca     180
ataaaatctc catctgtatt cagtacagat aaagtgtctg gatggatctg ccatgcagct     240
gaatggaaaa caacttgtga ttatagatgg tatggacccc aatacatcac ccacagtatt     300
catccgatca gtcctaccat agatgaatgc aggagaatca ttcaaaggat tgcatcaggg     360
actgatgaag atctggggtt tccccctcaa agttgcggat gggcatctgt cacaacggtg     420
tcaaatacta attatagagt agtaccccat tctgttcatt tagagccata cggaggacat     480
tggatcgatc acgaatttaa tgggggcgaa tgcagagaaa aagtgtgcga aatgaaaggg     540
aatcactcta tttggatcac agaggagact gtacagcatg agtgtgcaaa acatatagag     600
gaagttgaag gaattatgta cggaatgtt ccaagagggg atgtaatgta tgctaacaac      660
tttattatag atagacatca cagagtatac agattcgggg gatcttgtca gatgaaattc     720
tgtaataaag atggtataaa attcgcgaga ggagactggg tagagaaaac agccggaaca     780
ttaacaacga ttcatgacaa tgtgcctaaa tgtgttgatg gaacgttggt ctccggtcac     840
cgccccggat tagacttgat tgacacagtc ttcaatttgg aaaatgtagt ggaatatact     900
ttgtgtgaag ggactaaaag gaaaatcaat aaacaagaga agctgacatc agtggatttg     960
agctatttgg ctccaagaat cggagggttc ggatcagtat ttagagtgag aaacggaaca    1020
ttagagagag ggagcactac ttatatcaag atcgaagtag agggacctat tgtcgactcg    1080
ttaaatggga cagaccctag aactaacgcc tcaagagtat tctgggatga ctgggagtta    1140
gatggcaata tataccaggg ttttaatggt gtatataaag ggaaagatgg gaagatccat    1200
atccctttga atatgataga atcaggaatc atagatgatg agcttcaaca tgctttccaa    1260
gccgatatta tccctcatcc tcattatgat gacgatgaaa tccgagagga tgatatattt    1320
ttcgataaca ctggagaaaa tggaaatcct gtagatgcag tggtagaatg ggttagtgga    1380
tggggaacta gtctaaagtt ctttggcatg actctggtcg ccctgatcct gatctttctt    1440
ctcatcagat gctgtgttgc ttgcacttat ttgatgaaga ggagtaaact gcctgcaaca    1500
gaatcacacg aaatgcggtc tttagtttga                                    1530

<210> SEQ ID NO 32
<211> LENGTH: 509
<212> TYPE: PRT
<213> ORGANISM: Spring Viremia of Carp Virus (SVCV)
<300> PUBLICATION INFORMATION:
<308> DATABASE ACCESSION NUMBER: Genbank/NP_116747
<309> DATABASE ENTRY DATE: 2006-05-16

<400> SEQUENCE: 32
```

-continued

```
Met Ser Ile Ile Ser Tyr Ile Ala Phe Leu Leu Ile Asp Ser Asn
1               5                   10                  15

Leu Gly Ile Pro Ile Phe Val Pro Ser Gly Arg Asn Ile Ser Trp Gln
            20                  25                  30

Pro Val Ile Gln Pro Phe Asp Tyr Gln Cys Pro Ile His Gly Asn Leu
                35                  40                  45

Pro Asn Thr Met Gly Leu Ser Ala Thr Lys Leu Thr Ile Lys Ser Pro
    50                  55                  60

Ser Val Phe Ser Thr Asp Lys Val Ser Gly Trp Ile Cys His Ala Ala
65                  70                  75                  80

Glu Trp Lys Thr Thr Cys Asp Tyr Arg Trp Tyr Gly Pro Gln Tyr Ile
                85                  90                  95

Thr His Ser Ile His Pro Ile Ser Pro Thr Ile Asp Glu Cys Arg Arg
                100                 105                 110

Ile Ile Gln Arg Ile Ala Ser Gly Thr Asp Glu Asp Leu Gly Phe Pro
            115                 120                 125

Pro Gln Ser Cys Gly Trp Ala Ser Val Thr Thr Val Ser Asn Thr Asn
    130                 135                 140

Tyr Arg Val Val Pro His Ser Val His Leu Glu Pro Tyr Gly Gly His
145                 150                 155                 160

Trp Ile Asp His Glu Phe Asn Gly Gly Glu Cys Arg Glu Lys Val Cys
                165                 170                 175

Glu Met Lys Gly Asn His Ser Ile Trp Ile Thr Glu Thr Val Gln
                180                 185                 190

His Glu Cys Ala Lys His Ile Glu Glu Val Gly Ile Met Tyr Gly
            195                 200                 205

Asn Val Pro Arg Gly Asp Val Met Tyr Ala Asn Asn Phe Ile Ile Asp
210                 215                 220

Arg His His Arg Val Tyr Arg Phe Gly Gly Ser Cys Gln Met Lys Phe
225                 230                 235                 240

Cys Asn Lys Asp Gly Ile Lys Phe Ala Arg Gly Asp Trp Val Glu Lys
                245                 250                 255

Thr Ala Gly Thr Leu Thr Thr Ile His Asp Asn Val Pro Lys Cys Val
                260                 265                 270

Asp Gly Thr Leu Val Ser Gly His Arg Pro Gly Leu Asp Leu Ile Asp
            275                 280                 285

Thr Val Phe Asn Leu Glu Asn Val Val Glu Tyr Thr Leu Cys Glu Gly
            290                 295                 300

Thr Lys Arg Lys Ile Asn Lys Gln Glu Lys Leu Thr Ser Val Asp Leu
305                 310                 315                 320

Ser Tyr Leu Ala Pro Arg Ile Gly Gly Phe Gly Ser Val Phe Arg Val
                325                 330                 335

Arg Asn Gly Thr Leu Glu Arg Gly Ser Thr Thr Tyr Ile Lys Ile Glu
            340                 345                 350

Val Glu Gly Pro Ile Val Asp Ser Leu Asn Gly Thr Asp Pro Arg Thr
            355                 360                 365

Asn Ala Ser Arg Val Phe Trp Asp Asp Trp Glu Leu Asp Gly Asn Ile
    370                 375                 380

Tyr Gln Gly Phe Asn Gly Val Tyr Lys Gly Lys Asp Gly Lys Ile His
385                 390                 395                 400

Ile Pro Leu Asn Met Ile Glu Ser Gly Ile Ile Asp Asp Glu Leu Gln
                405                 410                 415

His Ala Phe Gln Ala Asp Ile Ile Pro His Pro His Tyr Asp Asp Asp
            420                 425                 430
```

```
Glu Ile Arg Glu Asp Asp Ile Phe Phe Asp Asn Thr Gly Glu Asn Gly
            435                 440                 445

Asn Pro Val Asp Ala Val Val Glu Trp Val Ser Gly Trp Gly Thr Ser
450                 455                 460

Leu Lys Phe Phe Gly Met Thr Leu Val Ala Leu Ile Leu Ile Phe Leu
465                 470                 475                 480

Leu Ile Arg Cys Cys Val Ala Cys Thr Tyr Leu Met Lys Arg Ser Lys
            485                 490                 495

Leu Pro Ala Thr Glu Ser His Glu Met Arg Ser Leu Val
            500                 505

<210> SEQ ID NO 33
<211> LENGTH: 1257
<212> TYPE: DNA
<213> ORGANISM: Spring Viremia of Carp Virus (SVCV)
<300> PUBLICATION INFORMATION:
<308> DATABASE ACCESSION NUMBER: Genbank/NC_002803
<309> DATABASE ENTRY DATE: 2006-05-16
<313> RELEVANT RESIDUES IN SEQ ID NO: (70)...(1326)

<400> SEQUENCE: 33
atgagtgtca ttcggatcaa acaaatgct accgttgctg ccgtgcttcc agctagcgaa      60
gatcaggccg attatccttc cacctttttt gaagggggga atgagattag attgtatgtt     120
aacaaggagg aaaaattgga tgttttaagg caatatgtct atatgggact ggtggagaaa     180
aactgtaaga tacagcatgt gaatgcttat ctctatgcag tgctgaaagg agaaagggag     240
ctgctagagg cggactggga tagcttcgga cacaagattg ggattcaggg agagaagatc     300 gggccttta acctggtgcg agtggaagac atccccgacg gctaccaga tgggaaactg       360 aacgctgagg tgagtgctga ggatgatgca tggctgcctc tcttcttgct aggtctctac     420
agagtgggaa gggcaagtga gactacatac cggactttgc tgatggaatc cctgataaaa    480
cagtgtaaag caataaaatc cgactgggtc tcccctgtga cggcaactca caaatatttc     540
gatgtatggg gcaatgatgg gaattacctg aagattgtag cctgtgtgga catgttttac    600
aaccatttca aaagagcat taagcaaca ttccggtggg gaacaattgt gtcacggttc      660
aaagactgtg cagcactcgc cacctggga catgttgtta aaatcaccgg tttgacaatt     720
gaagaagtgt ttacatgggt actacagact gaagtcgctg aagagttggt taaaatgatg    780
aagcctggac aggagataga taacagcgcg tcttacatgc catacctgat tgatatgggg    840
atctctgcca atcaccata tcaacaata aagaatccgt cttccactt ctgggggcag      900 cttgttgctg cattatgccg ctccaagaga gcactgaacg caagacagcc tgacgagatc     960
gactcaatgt cgatctcaaa tgcaagcttg ctgatggctt acgccttagg tagcagccct    1020
gatattgagc agcaattcag cacaggagac acatacagaa aaccgccaaa agaggcttcg    1080
tacctggtga gtgaggagcc aaaaagtcga tctgtcgttg aatggatcgc atggtattct    1140
gacgtagaca caaacccac ggatgacatg ctcatgatgg caaaaagagt agcagggact    1200
atctcagggc tcgtgataa ctcagtgggc aaatggataa acaaaccta tggataa        1257

<210> SEQ ID NO 34
<211> LENGTH: 418
<212> TYPE: PRT
<213> ORGANISM: Spring Viremia of Carp Virus (SVCV)
<300> PUBLICATION INFORMATION:
<308> DATABASE ACCESSION NUMBER: Genbank/NP_116744
<309> DATABASE ENTRY DATE: 2006-05-16

<400> SEQUENCE: 34
```

```
Met Ser Val Ile Arg Ile Lys Thr Asn Ala Thr Val Ala Ala Val Leu
1               5                   10                  15

Pro Ala Ser Glu Asp Gln Ala Asp Tyr Pro Ser Thr Phe Phe Glu Gly
            20                  25                  30

Gly Asn Glu Ile Arg Leu Tyr Val Asn Lys Glu Lys Leu Asp Val
            35                  40                  45

Leu Arg Gln Tyr Val Tyr Met Gly Leu Val Lys Asn Cys Lys Ile
    50                  55                  60

Gln His Val Asn Ala Tyr Leu Tyr Ala Val Leu Lys Gly Glu Arg Glu
65                  70                  75                  80

Leu Leu Glu Ala Asp Trp Asp Ser Phe Gly His Lys Ile Gly Ile Gln
                85                  90                  95

Gly Glu Lys Ile Gly Pro Phe Asn Leu Arg Val Glu Asp Ile Pro
            100                 105                 110

Asp Gly Leu Pro Asp Gly Lys Leu Asn Ala Glu Val Ser Ala Glu Asp
            115                 120                 125

Asp Ala Trp Leu Pro Leu Phe Leu Leu Gly Leu Tyr Arg Val Gly Arg
130                 135                 140

Ala Ser Glu Thr Thr Tyr Arg Thr Leu Leu Met Glu Ser Leu Ile Lys
145                 150                 155                 160

Gln Cys Lys Ala Ile Lys Ser Asp Trp Val Ser Pro Val Thr Ala Thr
                165                 170                 175

His Lys Tyr Phe Asp Val Trp Gly Asn Asp Gly Asn Tyr Leu Lys Ile
                180                 185                 190

Val Ala Cys Val Asp Met Phe Tyr Asn His Phe Lys Lys Ser Ile Lys
                195                 200                 205

Ala Thr Phe Arg Trp Gly Thr Ile Val Ser Arg Phe Lys Asp Cys Ala
            210                 215                 220

Ala Leu Ala Thr Leu Gly His Val Val Lys Ile Thr Gly Leu Thr Ile
225                 230                 235                 240

Glu Glu Val Phe Thr Trp Val Leu Gln Thr Glu Val Ala Glu Glu Leu
                245                 250                 255

Val Lys Met Met Lys Pro Gly Gln Glu Ile Asp Asn Ser Ala Ser Tyr
            260                 265                 270

Met Pro Tyr Leu Ile Asp Met Gly Ile Ser Ala Lys Ser Pro Tyr Ser
            275                 280                 285

Thr Ile Lys Asn Pro Ser Phe His Phe Trp Gly Gln Leu Val Ala Ala
            290                 295                 300

Leu Cys Arg Ser Lys Arg Ala Leu Asn Ala Arg Gln Pro Asp Glu Ile
305                 310                 315                 320

Asp Ser Met Ser Ile Ser Asn Ala Ser Leu Leu Met Ala Tyr Ala Leu
                325                 330                 335

Gly Ser Ser Pro Asp Ile Glu Gln Gln Phe Ser Thr Gly Asp Thr Tyr
            340                 345                 350

Arg Lys Pro Pro Lys Glu Ala Ser Tyr Leu Val Ser Glu Glu Pro Lys
            355                 360                 365

Ser Arg Ser Val Val Glu Trp Ile Ala Trp Tyr Ser Asp Val Asp Asn
            370                 375                 380

Lys Pro Thr Asp Asp Met Leu Met Met Ala Lys Arg Val Ala Gly Thr
385                 390                 395                 400

Ile Ser Gly Pro Arg Asp Asn Ser Val Gly Lys Trp Ile Lys Gln Thr
                405                 410                 415

Tyr Gly
```

<210> SEQ ID NO 35
<211> LENGTH: 1524
<212> TYPE: DNA
<213> ORGANISM: Viral Hemorrhagic Septicemia Virus (VHSV)
<300> PUBLICATION INFORMATION:
<308> DATABASE ACCESSION NUMBER: Genbank/NC_000855
<309> DATABASE ENTRY DATE: 2006-10-21
<313> RELEVANT RESIDUES IN SEQ ID NO: (2959)...(4482)

<400> SEQUENCE: 35

```
atggaatgga acacttttt cttggtcatc ttgatcatca tcataaagag caccacacca        60
cagatcactc aacgacctcc ggtcgaaaac atctcgacgt accatgcaga ttgggacact       120
ccgctataca ctcatccctc caactgcagg gacgattcct ttgtcccgat tcgaccagct       180
caactcaggt gtcctcatga atttgaagac ataaacaagg gactggtctc cgtcccaacc       240
aagatcatcc atctcccgct atcagtcacc agcgtctccg cagtcgcgag tggccactac       300
ctgcacagag tgacttatcg agtcacctgt tcgaccagct tctttggagg gcaaaccatt       360
gaaaagacca tcttagaggc gaaactgtct cgtcaggagg ccacagacga ggcaagcaag       420
gatcacgagt acccgttctt ccctgaaccc tcctgcatct ggatgaaaaa caatgtccat       480
aaggacataa ctcactatta caagacccca aaaacagtat cggtggatct ctacagcagg       540
aaatttctca accctgattt catagagggg gtttgcacaa cctcgccctg tcaaactcat       600
tggcagggag tctattgggt cggtgccaca cccaaagccc attgccccac gtcggaaaca       660
ctagaaggac acctgttcac caggacccat gatcacaggg tggtcaaggc aattgtggca       720
ggccatcatc cctggggact cacaatggca tgcacagtga cattctgcgg ggcagaatgg       780
atcaagactg acctgggaga cctgatccag gtaacaggac cggggggcac ggggaaactg       840
actccaaaga agtgtgtcaa tgctgatgtc cagatgaggg gggcaacaga tgacttttct       900
tatctcaacc atctcatcac caacatggct caaagaaccg agtgcctaga tgcccatagt       960
gatatcaccg cttctgggaa aatatcctca tttctcctct caaagtttcg tcccagccac      1020
cctggacccg gcaaggcaca ctatcttctc aacggtcaaa tcatgcgagg tgactgtgac      1080
tatgaggcag tagtcagcat caactacaac agcgctcaat acaagacagt gaacaacaca      1140
tggaaatcat ggaaacgggt agacaacaac acagacgggt acgatgggat gatatttggg      1200
gacaaattga tcatcccgga catcgagaag tatcagagtg tctatgacag tggaatgctc      1260
gttcaaagaa accttgtgga agtccctcat ctgagcattg tgtttgtctc caacacatct      1320
gatctttcca ctaatcacat ccacaccaac ctaatcccct cggattggtc attccactgg      1380
agtatttggc cctcattatc tgggatgggg gttgtgggag gggccttcct tctactggta      1440
ctctgctgtt gctgcaaggc gtcccctccc attccaaatt acgggattcc gatgcagcag      1500
ttctccagaa gtcagacggt ctga                                            1524
```

<210> SEQ ID NO 36
<211> LENGTH: 507
<212> TYPE: PRT
<213> ORGANISM: Viral Hemorrhagic Septicemia Virus (VHSV)
<300> PUBLICATION INFORMATION:
<308> DATABASE ACCESSION NUMBER: Genbank/NP_049548
<309> DATABASE ENTRY DATE: 2006-10-21

<400> SEQUENCE: 36

```
Met Glu Trp Asn Thr Phe Phe Leu Val Ile Leu Ile Ile Ile Ile Lys
1               5                   10                  15

Ser Thr Thr Pro Gln Ile Thr Gln Arg Pro Pro Val Glu Asn Ile Ser
```

```
                    20                  25                  30
Thr Tyr His Ala Asp Trp Asp Thr Pro Leu Tyr Thr His Pro Ser Asn
                    35                  40                  45

Cys Arg Asp Asp Ser Phe Val Pro Ile Arg Pro Ala Gln Leu Arg Cys
                    50                  55                  60

Pro His Glu Phe Glu Asp Ile Asn Lys Gly Leu Val Ser Val Pro Thr
 65                  70                  75                  80

Lys Ile Ile His Leu Pro Leu Ser Val Thr Ser Val Ser Ala Val Ala
                    85                  90                  95

Ser Gly His Tyr Leu His Arg Val Thr Tyr Arg Val Thr Cys Ser Thr
                    100                 105                 110

Ser Phe Phe Gly Gly Gln Thr Ile Glu Lys Thr Ile Leu Glu Ala Lys
                    115                 120                 125

Leu Ser Arg Gln Glu Ala Thr Asp Glu Ala Ser Lys Asp His Glu Tyr
                    130                 135                 140

Pro Phe Phe Pro Glu Pro Ser Cys Ile Trp Met Lys Asn Asn Val His
145                 150                 155                 160

Lys Asp Ile Thr His Tyr Tyr Lys Thr Pro Lys Thr Val Ser Val Asp
                    165                 170                 175

Leu Tyr Ser Arg Lys Phe Leu Asn Pro Asp Phe Ile Glu Gly Val Cys
                    180                 185                 190

Thr Thr Ser Pro Cys Gln Thr His Trp Gln Gly Val Tyr Trp Val Gly
                    195                 200                 205

Ala Thr Pro Lys Ala His Cys Pro Thr Ser Glu Thr Leu Glu Gly His
                    210                 215                 220

Leu Phe Thr Arg Thr His Asp His Arg Val Val Lys Ala Ile Val Ala
225                 230                 235                 240

Gly His His Pro Trp Gly Leu Thr Met Ala Cys Thr Val Thr Phe Cys
                    245                 250                 255

Gly Ala Glu Trp Ile Lys Thr Asp Leu Gly Asp Leu Ile Gln Val Thr
                    260                 265                 270

Gly Pro Gly Gly Thr Gly Lys Leu Thr Pro Lys Lys Cys Val Asn Ala
                    275                 280                 285

Asp Val Gln Met Arg Gly Ala Thr Asp Phe Ser Tyr Leu Asn His
                    290                 295                 300

Leu Ile Thr Asn Met Ala Gln Arg Thr Glu Cys Leu Asp Ala His Ser
305                 310                 315                 320

Asp Ile Thr Ala Ser Gly Lys Ile Ser Ser Phe Leu Leu Ser Lys Phe
                    325                 330                 335

Arg Pro Ser His Pro Gly Pro Gly Lys Ala His Tyr Leu Leu Asn Gly
                    340                 345                 350

Gln Ile Met Arg Gly Asp Cys Asp Tyr Glu Ala Val Val Ser Ile Asn
                    355                 360                 365

Tyr Asn Ser Ala Gln Tyr Lys Thr Val Asn Asn Thr Trp Lys Ser Trp
                    370                 375                 380

Lys Arg Val Asp Asn Asn Thr Asp Gly Tyr Asp Gly Met Ile Phe Gly
385                 390                 395                 400

Asp Lys Leu Ile Ile Pro Asp Ile Glu Lys Tyr Gln Ser Val Tyr Asp
                    405                 410                 415

Ser Gly Met Leu Val Gln Arg Asn Leu Val Glu Val Pro His Leu Ser
                    420                 425                 430

Ile Val Phe Val Ser Asn Thr Ser Asp Leu Ser Thr Asn His Ile His
                    435                 440                 445
```

```
       Thr Asn Leu Ile Pro Ser Asp Trp Ser Phe His Trp Ser Ile Trp Pro
           450                 455                 460

Ser Leu Ser Gly Met Gly Val Val Gly Gly Ala Phe Leu Leu Leu Val
       465                 470                 475                 480

Leu Cys Cys Cys Cys Lys Ala Ser Pro Pro Ile Pro Asn Tyr Gly Ile
                           485                 490                 495

Pro Met Gln Gln Phe Ser Arg Ser Gln Thr Val
                       500                 505

<210> SEQ ID NO 37
<211> LENGTH: 1215
<212> TYPE: DNA
<213> ORGANISM: Viral Hemorrhagic Septicemia Virus (VHSV)
<300> PUBLICATION INFORMATION:
<308> DATABASE ACCESSION NUMBER: Genbank/NC_000855
<309> DATABASE ENTRY DATE: 2006-10-21
<313> RELEVANT RESIDUES IN SEQ ID NO: (168)...(1382)

<400> SEQUENCE: 37
atggaaggag gacttcgtgc agcgttttca ggcctgaatg aggttaggat cgaccccacc       60
ggtggagagg gacgggtact tgtacctggt gacgtggagc tcatcgtgta tgttggtgga      120
tttggtgagg aagacaggaa ggtgattgtg gatgcactct ccgcactcgg ggaccccag      180 actgtacagg cgttgtccgt gcttctctcc tatgtactcc aagggaacac acaggaggac      240
ctagaaacaa agtgcaaggt cctcacagac atgggcttca aggtgacaca ggcagtcagg      300
gccacgagca tcgaggcggg aatcatgatg cccatgagag aactggccct gactgtcaat      360
gacgacaacc tcatggaaat cgtcaagggg accttgatga catgctccct tcttaccaag      420
tactcggtgg acaagatgat caagtacatc actaagaaac tcggggagct ggcagacacc      480
cagggagttg gggaactgca gcacttcacc gctgacaagg cagccatcag gaaactcgca      540
gggtgtgtgc gtcccgggca aagatcacc aaggccctct atgcgttcat cctgaccgag      600
atcgcagacc ccaccaccca gtcgagggcc cgagcaatgg gggcgttgag gctcaacggg      660
acaggaatga ccatgattgg gttgttcacc caggccgcca acaacttggg cattgccccg      720
gcaaagctgc tggaggacct ctgcatggag tccctggttg agtcagccag acggatcatc      780
cagttgatga cacaggtgtc agaggcgaag tccatccaag agcgctacgc catcatgatg      840
agtcggatgc tgggagagtc ctactacaag tcgtatggac tcaatgacaa ctccaagatc      900
tcttacattc tgtcacagat tagtgggaag tacgcagtgg actccctgga aggcctggag      960
gggatcaagg tgacagagaa gttccgcgag ttcgctgagc ttgttgcaga agtcctggtg     1020
gacaagtacg agaggattgg agaggacagc acggaggtct cagatgtcat caaggaggcg     1080
accagacagc acgcgcgcag gacatctgcc aagccagagc caaggcccg caacttcagg     1140 agctccaccg gaaggggaa ggagcaggag acggggagt ccgatgatga cgactacccc     1200
gaggactctg actaa                                                      1215

<210> SEQ ID NO 38
<211> LENGTH: 404
<212> TYPE: PRT
<213> ORGANISM: Viral Hemorrhagic Septicemia Virus (VHSV)
<300> PUBLICATION INFORMATION:
<308> DATABASE ACCESSION NUMBER: Genbank/NP_049545
<309> DATABASE ENTRY DATE: 2006-10-21

<400> SEQUENCE: 38

Met Glu Gly Gly Leu Arg Ala Ala Phe Ser Gly Leu Asn Glu Val Arg
1               5                   10                  15
```

Ile Asp Pro Thr Gly Gly Glu Gly Arg Val Leu Val Pro Gly Asp Val
            20                  25                  30

Glu Leu Ile Val Tyr Val Gly Phe Gly Glu Asp Arg Lys Val
        35                  40                  45

Ile Val Asp Ala Leu Ser Ala Leu Gly Gly Pro Gln Thr Val Gln Ala
 50                  55                  60

Leu Ser Val Leu Ser Tyr Val Leu Gln Gly Asn Thr Gln Glu Asp
 65                  70                  75                  80

Leu Glu Thr Lys Cys Lys Val Leu Thr Asp Met Gly Phe Lys Val Thr
                 85                  90                  95

Gln Ala Val Arg Ala Thr Ser Ile Glu Ala Gly Ile Met Met Pro Met
                100                 105                 110

Arg Glu Leu Ala Leu Thr Val Asn Asp Asp Asn Leu Met Glu Ile Val
                115                 120                 125

Lys Gly Thr Leu Met Thr Cys Ser Leu Leu Thr Lys Tyr Ser Val Asp
                130                 135                 140

Lys Met Ile Lys Tyr Ile Thr Lys Lys Leu Gly Glu Leu Ala Asp Thr
145                 150                 155                 160

Gln Gly Val Gly Glu Leu Gln His Phe Thr Ala Asp Lys Ala Ala Ile
                165                 170                 175

Arg Lys Leu Ala Gly Cys Val Arg Pro Gly Gln Lys Ile Thr Lys Ala
                180                 185                 190

Leu Tyr Ala Phe Ile Leu Thr Glu Ile Ala Asp Pro Thr Thr Gln Ser
                195                 200                 205

Arg Ala Arg Ala Met Gly Ala Leu Arg Leu Asn Gly Thr Gly Met Thr
                210                 215                 220

Met Ile Gly Leu Phe Thr Gln Ala Ala Asn Asn Leu Gly Ile Ala Pro
225                 230                 235                 240

Ala Lys Leu Leu Glu Asp Leu Cys Met Glu Ser Leu Val Glu Ser Ala
                245                 250                 255

Arg Arg Ile Ile Gln Leu Met Arg Gln Val Ser Glu Ala Lys Ser Ile
                260                 265                 270

Gln Glu Arg Tyr Ala Ile Met Met Ser Arg Met Leu Gly Glu Ser Tyr
                275                 280                 285

Tyr Lys Ser Tyr Gly Leu Asn Asp Asn Ser Lys Ile Ser Tyr Ile Leu
                290                 295                 300

Ser Gln Ile Ser Gly Lys Tyr Ala Val Asp Ser Leu Glu Gly Leu Glu
305                 310                 315                 320

Gly Ile Lys Val Thr Glu Lys Phe Arg Glu Phe Ala Glu Leu Val Ala
                325                 330                 335

Glu Val Leu Val Asp Lys Tyr Gly Arg Ile Gly Glu Ser Thr Glu
                340                 345                 350

Val Ser Asp Val Ile Lys Glu Ala Thr Arg Gln His Ala Arg Arg Thr
                355                 360                 365

Ser Ala Lys Pro Glu Pro Lys Ala Arg Asn Phe Arg Ser Ser Thr Gly
                370                 375                 380

Arg Gly Lys Glu Gln Glu Thr Gly Glu Ser Asp Asp Asp Tyr Pro
385                 390                 395                 400

Glu Asp Ser Asp

<210> SEQ ID NO 39
<211> LENGTH: 1383
<212> TYPE: DNA
<213> ORGANISM: Salmon pancreas disease virus (PDV)
<300> PUBLICATION INFORMATION:

<308> DATABASE ACCESSION NUMBER: Genbank/AJ316244
<309> DATABASE ENTRY DATE: 2005-04-15
<313> RELEVANT RESIDUES IN SEQ ID NO: (10446)...(11828)

<400> SEQUENCE: 39

```
tacgaacaca ccgtggtggt cccaatggat ccaagagccc cgtcgtacga agcagtgata     60
aaccggaatg ggtatgatcc attgaagctg accatctcag tgaatttcac cgtcatctca    120
ccaactacgg ctctggaata ttggacctgc gcaggagtcc ccatcgtcga gccgccccat    180
gtgggctgct gcacgtcggt gtcctgcccc tctgacctct ctacgctgca tgcgtttact    240
ggcaaagctg tctccgacgt gcactgcgat gtgcacacaa acgtgtaccc cttgttgtgg    300
ggcgcggctc actgcttctg ttccaccgag aatacacagg tcagcgctgt ggcagccacc    360
gtttctgagt tctgtgccca ggactcagag cgtgccgaag cgttcagcgt acacagcagc    420
tcagtcaccg ctgaggtcct ggtgacgctt ggtgaagtgg tgacggcagt ccacgtttac    480
gtggacgggg taacatcagc caggggcact gacctcaaga tcgtggctgg accaataaca    540
accgactact ccccattcga tcgcaaagta gtccgcatcg gcgaagaggt ctataactat    600
gactggcctc cttacggggc tggccgacca ggcacattcg gagacattca gctaggtca     660
accaactatg tcaaacccaa cgatctgtat ggggacatcg gaattgaagt actgcagccg    720
actaacgacc acgtacatgt ggcttacacg tatacgacct ctgggttact gcgttggctg    780
caggacgctc cgaaaccact cagtgtcaca gcaccgcacg gttgtaagat cagtgccaat    840
ccgctcctgg ccctcgattg tggggttggt gccgtcccca tgtccatcaa cattccggac    900
gcgaagttta cccgcaaatt aaaggatccg aaaccatcgg ccctgaaatg cgtggtggac    960
agctgcgagt acggggtgga ctacgggggc gccgccacga tcacctacga gggccacgag   1020
gccgggaagt gcgggattca ttccctgaca ccaggagtcc ccctgagaac atcggtggtt   1080
gaagtggttg ctggcgccaa taccgtcaaa acgaccttct cctcaccac gcccgaggtt    1140
gcactcgagg tagagatctg ttcggcaata gtgaagtgcg ctggtgagtg cactccaccg   1200
aaggaacatg tggtcgcaac caggcctcgc catggcagcg accctggagg ctacatctcc   1260
gggcccgcaa tgcgctgggc cggagggatt gtagggaccc tagtggtcct gttccttatc   1320
cttgccgtca tctactgcgt ggtgaagaag tgccgctcca aaagaatccg gatagtcaag   1380
agc                                                                 1383
```

<210> SEQ ID NO 40
<211> LENGTH: 461
<212> TYPE: PRT
<213> ORGANISM: Salmon pancreas disease virus (PDV)
<300> PUBLICATION INFORMATION:
<308> DATABASE ACCESSION NUMBER: Genbank/CAC87722
<309> DATABASE ENTRY DATE: 2005-04-15

<400> SEQUENCE: 40

```
Tyr Glu His Thr Val Val Pro Met Asp Pro Arg Ala Pro Ser Tyr
1               5                   10                  15

Glu Ala Val Ile Asn Arg Asn Gly Tyr Asp Pro Leu Lys Leu Thr Ile
            20                  25                  30

Ser Val Asn Phe Thr Val Ile Ser Pro Thr Thr Ala Leu Glu Tyr Trp
        35                  40                  45

Thr Cys Ala Gly Val Pro Ile Val Glu Pro Pro His Val Gly Cys Cys
    50                  55                  60

Thr Ser Val Ser Cys Pro Ser Asp Leu Ser Thr Leu His Ala Phe Thr
65                  70                  75                  80
```

```
Gly Lys Ala Val Ser Asp Val His Cys Asp Val His Thr Asn Val Tyr
             85                  90                  95

Pro Leu Leu Trp Gly Ala Ala His Cys Phe Cys Ser Thr Glu Asn Thr
            100                 105                 110

Gln Val Ser Ala Val Ala Thr Val Ser Glu Phe Cys Ala Gln Asp
        115                 120                 125

Ser Glu Arg Ala Glu Ala Phe Ser Val His Ser Ser Val Thr Ala
    130                 135                 140

Glu Val Leu Val Thr Leu Gly Glu Val Thr Ala Val His Val Tyr
145                 150                 155                 160

Val Asp Gly Val Thr Ser Ala Arg Gly Thr Asp Leu Lys Ile Val Ala
                165                 170                 175

Gly Pro Ile Thr Thr Asp Tyr Ser Pro Phe Asp Arg Lys Val Val Arg
            180                 185                 190

Ile Gly Glu Glu Val Tyr Asn Tyr Asp Trp Pro Pro Tyr Gly Ala Gly
            195                 200                 205

Arg Pro Gly Thr Phe Gly Asp Ile Gln Ala Arg Ser Thr Asn Tyr Val
    210                 215                 220

Lys Pro Asn Asp Leu Tyr Gly Asp Ile Gly Ile Glu Val Leu Gln Pro
225                 230                 235                 240

Thr Asn Asp His Val His Val Ala Tyr Thr Tyr Thr Thr Ser Gly Leu
                245                 250                 255

Leu Arg Trp Leu Gln Asp Ala Pro Lys Pro Leu Ser Val Thr Ala Pro
            260                 265                 270

His Gly Cys Lys Ile Ser Ala Asn Pro Leu Leu Ala Leu Asp Cys Gly
            275                 280                 285

Val Gly Ala Val Pro Met Ser Ile Asn Ile Pro Asp Ala Lys Phe Thr
290                 295                 300

Arg Lys Leu Lys Asp Pro Lys Pro Ser Ala Leu Lys Cys Val Val Asp
305                 310                 315                 320

Ser Cys Glu Tyr Gly Val Asp Tyr Gly Gly Ala Ala Thr Ile Thr Tyr
                325                 330                 335

Glu Gly His Glu Ala Gly Lys Cys Gly Ile His Ser Leu Thr Pro Gly
            340                 345                 350

Val Pro Leu Arg Thr Ser Val Val Glu Val Ala Gly Ala Asn Thr
            355                 360                 365

Val Lys Thr Thr Phe Ser Ser Pro Thr Pro Glu Val Ala Leu Glu Val
    370                 375                 380

Glu Ile Cys Ser Ala Ile Val Lys Cys Ala Gly Glu Cys Thr Pro Pro
385                 390                 395                 400

Lys Glu His Val Val Ala Thr Arg Pro Arg His Gly Ser Asp Pro Gly
                405                 410                 415

Gly Tyr Ile Ser Gly Pro Ala Met Arg Trp Ala Gly Gly Ile Val Gly
            420                 425                 430

Thr Leu Val Val Leu Phe Leu Ile Leu Ala Val Ile Tyr Cys Val Val
            435                 440                 445

Lys Lys Cys Arg Ser Lys Arg Ile Arg Ile Val Lys Ser
450                 455                 460

<210> SEQ ID NO 41
<211> LENGTH: 1314
<212> TYPE: DNA
<213> ORGANISM: Salmon pancreas disease virus (PDV)
<300> PUBLICATION INFORMATION:
<308> DATABASE ACCESSION NUMBER: Genbank/AJ316244
<309> DATABASE ENTRY DATE: 2005-04-15
```

<313> RELEVANT RESIDUES IN SEQ ID NO: (8928)...(10241)

<400> SEQUENCE: 41

```
gctgtgtcta cgtcgcctgc cgccttttac gacacacaga tcctcgccgc ccacgcagct      60
gcctccccat acagggcgta ctgccccgat tgtgacggaa cagcgtgtat ctcgccgata     120
gccatcgacg aggtggtgag cagtggcagc gaccacgtcc tccgcatgcg ggttggttct     180
caatcgggag tgaccgctaa gggtggtgcg gcgggtgaaa cctctctgcg ataccctggga    240
agggacggga aggttcacgc cgcagacaac acgcgactcg tggtgcgcac gactgcaaag     300
tgcgacgtgc tgcaggccac tggccactac atcctggcca actgcccagt ggggcagagc     360
ctaaccgttg cggccacact ggatggcacc cggcatcaat gcaccacggt tttcgaacac     420
caagtaacgg agaagttcac cagagaacgc agcaagggcc accatctgtc cgacatgacc     480
aagaaatgca ccagatttc cactacacca aaaagtccg ccctctacct cgttgatgtg       540
tatgacgctc tgccgatttc tgtagagatt agcaccgtcg taacatgcag cgacagccag     600
tgcacagtga gggtgccacc tggtaccaca gtgaaattcg acaagaaatg caagagcgct     660
gactcggcaa ccgtcacttt caccagcgac tcccagacgt ttacgtgtga ggagccagtc     720
ctaacggctg ccagtatcac ccagggcaag ccacacctca gatcggcaat gttgcctagc     780
ggaggcaagg aagtgaaagc aaggatcccg ttcccgttcc cgccggaaac cgcaacttgc     840
agagtgagtg tagcccccact gccgtcgatc acctacgagg aaagcgatgt cctgctagcc    900
ggtaccgcaa ataccctgt gctgctaacc acacggaacc ttggtttcca tagcaacgcc     960
acatccgaat ggatccaggg caagtacctg cgccgcatcc cggtcacgcc tcaagggatc   1020
gagctaacat ggggaaacaa cgcgccgatg cacttttggt catccgtcag gtacgcatcc   1080
ggggacgctg atgcgtaccc ctgggaactt ctggtgtacc acaccaagca ccatccagag   1140
tacgcgtggg cgtttgtagg agttgcatgc ggcctgctgg ctatcgcagc gtgcatgttt   1200
gcgtgcgcat gcagcagggt gcggtactct ctggtcgcca acacgttcaa ctcgaacccca   1260
ccaccattga ccgcactgac tgcagcactg tgttgcatac caggggctcg cgcg          1314
```

<210> SEQ ID NO 42
<211> LENGTH: 438
<212> TYPE: PRT
<213> ORGANISM: Salmon pancreas disease virus (PDV)
<300> PUBLICATION INFORMATION:
<308> DATABASE ACCESSION NUMBER: Genbank/CAC87722
<309> DATABASE ENTRY DATE: 2005-04-15

<400> SEQUENCE: 42

Ala Val Ser Thr Ser Pro Ala Ala Phe Tyr Asp Thr Gln Ile Leu Ala
1 5 10 15

Ala His Ala Ala Ala Ser Pro Tyr Arg Ala Tyr Cys Pro Asp Cys Asp
20 25 30

Gly Thr Ala Cys Ile Ser Pro Ile Ala Ile Asp Glu Val Val Ser Ser
35 40 45

Gly Ser Asp His Val Leu Arg Met Arg Val Gly Ser Gln Ser Gly Val
50 55 60

Thr Ala Lys Gly Gly Ala Ala Gly Glu Thr Ser Leu Arg Tyr Leu Gly
65 70 75 80

Arg Asp Gly Lys Val His Ala Ala Asp Asn Thr Arg Leu Val Val Arg
85 90 95

Thr Thr Ala Lys Cys Asp Val Leu Gln Ala Thr Gly His Tyr Ile Leu
100 105 110

| | | | | | | | | | | | |
|---|---|---|---|---|---|---|---|---|---|---|---|
|Ala|Asn|Cys|Pro|Val|Gly|Gln|Ser|Leu|Thr|Val|Ala|Ala|Thr|Leu|Asp|
| | |115| | | |120| | | |125| |

Gly Thr Arg His Gln Cys Thr Thr Val Phe Glu His Gln Val Thr Glu
    130                 135                 140

Lys Phe Thr Arg Glu Arg Ser Lys Gly His His Leu Ser Asp Met Thr
145                 150                 155                 160

Lys Lys Cys Thr Arg Phe Ser Thr Thr Pro Lys Lys Ser Ala Leu Tyr
                165                 170                 175

Leu Val Asp Val Tyr Asp Ala Leu Pro Ile Ser Val Glu Ile Ser Thr
                180                 185                 190

Val Val Thr Cys Ser Asp Ser Gln Cys Thr Val Arg Val Pro Pro Gly
                195                 200                 205

Thr Thr Val Lys Phe Asp Lys Lys Cys Lys Ser Ala Asp Ser Ala Thr
            210                 215                 220

Val Thr Phe Thr Ser Asp Ser Gln Thr Phe Thr Cys Glu Glu Pro Val
225                 230                 235                 240

Leu Thr Ala Ala Ser Ile Thr Gln Gly Lys Pro His Leu Arg Ser Ala
                245                 250                 255

Met Leu Pro Ser Gly Gly Lys Glu Val Lys Ala Arg Ile Pro Phe Pro
            260                 265                 270

Phe Pro Pro Glu Thr Ala Thr Cys Arg Val Ser Val Ala Pro Leu Pro
        275                 280                 285

Ser Ile Thr Tyr Glu Glu Ser Asp Val Leu Leu Ala Gly Thr Ala Lys
    290                 295                 300

Tyr Pro Val Leu Leu Thr Thr Arg Asn Leu Gly Phe His Ser Asn Ala
305                 310                 315                 320

Thr Ser Glu Trp Ile Gln Gly Lys Tyr Leu Arg Arg Ile Pro Val Thr
                325                 330                 335

Pro Gln Gly Ile Glu Leu Thr Trp Gly Asn Asn Ala Pro Met His Phe
            340                 345                 350

Trp Ser Ser Val Arg Tyr Ala Ser Gly Asp Ala Asp Ala Tyr Pro Trp
        355                 360                 365

Glu Leu Leu Val Tyr His Thr Lys His His Pro Glu Tyr Ala Trp Ala
    370                 375                 380

Phe Val Gly Val Ala Cys Gly Leu Leu Ala Ile Ala Ala Cys Met Phe
385                 390                 395                 400

Ala Cys Ala Cys Ser Arg Val Arg Tyr Ser Leu Val Ala Asn Thr Phe
                405                 410                 415

Asn Ser Asn Pro Pro Leu Thr Ala Leu Thr Ala Ala Leu Cys Cys
            420                 425                 430

Ile Pro Gly Ala Arg Ala
        435

<210> SEQ ID NO 43
<211> LENGTH: 213
<212> TYPE: DNA
<213> ORGANISM: Salmon pancreas disease virus (PDV)
<300> PUBLICATION INFORMATION:
<308> DATABASE ACCESSION NUMBER: Genbank/AJ316244
<309> DATABASE ENTRY DATE: 2005-04-15
<313> RELEVANT RESIDUES IN SEQ ID NO: (8715)...(8927)

<400> SEQUENCE: 43

```
acacgcgctc cggccctcct gctgctgcct atggttattg tctgcaccta caattccaac      60
accttcgatt gctccaaacc gtcctgccag gactgctgca ttactgctga accagagaag     120
gccatgacca tgctgaagga caatctgaac gacccgaact actgggacct actcattgct     180
```

```
gtcaccacct gtggctccgc ccggagaaag agg                                     213
```

<210> SEQ ID NO 44
<211> LENGTH: 71
<212> TYPE: PRT
<213> ORGANISM: Salmon pancreas disease virus (PDV)
<300> PUBLICATION INFORMATION:
<308> DATABASE ACCESSION NUMBER: Genbank/CAC87722
<309> DATABASE ENTRY DATE: 2005-04-15

<400> SEQUENCE: 44

Thr Arg Ala Pro Ala Leu Leu Leu Pro Met Val Ile Val Cys Thr
1               5                   10                  15

Tyr Asn Ser Asn Thr Phe Asp Cys Ser Lys Pro Ser Cys Gln Asp Cys
            20                  25                  30

Cys Ile Thr Ala Glu Pro Glu Lys Ala Met Thr Met Leu Lys Asp Asn
        35                  40                  45

Leu Asn Asp Pro Asn Tyr Trp Asp Leu Leu Ile Ala Val Thr Thr Cys
    50                  55                  60

Gly Ser Ala Arg Arg Lys Arg
65                  70

<210> SEQ ID NO 45
<211> LENGTH: 846
<212> TYPE: DNA
<213> ORGANISM: Salmon pancreas disease virus (PDV)
<300> PUBLICATION INFORMATION:
<308> DATABASE ACCESSION NUMBER: Genbank/AJ316244
<309> DATABASE ENTRY DATE: 2005-04-15
<313> RELEVANT RESIDUES IN SEQ ID NO: (7869)...(8714)

<400> SEQUENCE: 45

```
atgtttccca tgcaattcac caactcagcc tatcgccaga tggagcccat gtttgcaccg      60
ggttcccgag acaagtaca gccgtaccgg ccgcgcacta gcgccgcca ggagccgcaa       120
gtcggcaacg ccgccattac tgccctcgcg aaccagatga gtgcgctcca gttgcaggta    180
gctggacttg ccggccaggc aagggtggac cgccgtgggc aagacgtgt tcagaagaac     240
aagcagaaga agaagaactc ttccaacgga gaaaaccca aagagaagaa gaagaagcaa    300
aaacaacagg agaagaaggg aagcggtggc gaaaaagtca agaagactag gaaccgaccc   360
gggaaggagg taaggatctc cgtaaagtgt gcccgacaga gcaccttccc cgtgtaccac   420
gaaggtgcta tatccggcta cgctgtgctg attggatctc gcgtattcaa gccggcacac   480
gtgaagggta agatcgacca ccctgaactg gcagacatca agttccaggt cgccgaggac   540
atggacctcg aagcagctgc gtacccgaag agcatgcgag accaagcggc tgaaccagcg   600
accatgatgg acagagtgta caactgggag tatggcacta tcagagtgga ggataatgtc   660
ataatcgacg caagcggtag gggcaagccg ggtgacagtg gcagggccat caccgacaac   720
tcgggaaagg ttgttggtat tgtcctcgga ggaggacccg atggcaggcg cacacgcctc   780
tccgtgatag gtttcgacaa gaagatgaag gctagggaga tcgcctacag tgatgccata   840
ccttgg                                                              846
```

<210> SEQ ID NO 46
<211> LENGTH: 282
<212> TYPE: PRT
<213> ORGANISM: Salmon pancreas disease virus (PDV)
<300> PUBLICATION INFORMATION:
<308> DATABASE ACCESSION NUMBER: Genbank/CAC87722
<309> DATABASE ENTRY DATE:

<400> SEQUENCE: 46

```
Met Phe Pro Met Gln Phe Thr Asn Ser Ala Tyr Arg Gln Met Glu Pro
1               5                   10                  15
Met Phe Ala Pro Gly Ser Arg Gly Gln Val Gln Pro Tyr Arg Pro Arg
            20                  25                  30
Thr Lys Arg Arg Gln Glu Pro Gln Val Gly Asn Ala Ala Ile Thr Ala
        35                  40                  45
Leu Ala Asn Gln Met Ser Ala Leu Gln Leu Gln Val Ala Gly Leu Ala
    50                  55                  60
Gly Gln Ala Arg Val Asp Arg Arg Gly Pro Arg Arg Val Gln Lys Asn
65                  70                  75                  80
Lys Gln Lys Lys Lys Asn Ser Ser Asn Gly Glu Lys Pro Lys Glu Lys
                85                  90                  95
Lys Lys Lys Gln Lys Gln Gln Glu Lys Lys Gly Ser Gly Gly Glu Lys
                100                 105                 110
Val Lys Lys Thr Arg Asn Arg Pro Gly Lys Glu Val Arg Ile Ser Val
            115                 120                 125
Lys Cys Ala Arg Gln Ser Thr Phe Pro Val Tyr His Glu Gly Ala Ile
    130                 135                 140
Ser Gly Tyr Ala Val Leu Ile Gly Ser Arg Val Phe Lys Pro Ala His
145                 150                 155                 160
Val Lys Gly Lys Ile Asp His Pro Glu Leu Ala Asp Ile Lys Phe Gln
                165                 170                 175
Val Ala Glu Asp Met Asp Leu Gly Ala Ala Tyr Pro Lys Ser Met
                180                 185                 190
Arg Asp Gln Ala Ala Glu Pro Ala Thr Met Met Asp Arg Val Tyr Asn
            195                 200                 205
Trp Glu Tyr Gly Thr Ile Arg Val Glu Asp Asn Val Ile Ile Asp Ala
    210                 215                 220
Ser Gly Arg Gly Lys Pro Gly Asp Ser Gly Arg Ala Ile Thr Asp Asn
225                 230                 235                 240
Ser Gly Lys Val Val Gly Ile Val Leu Gly Gly Pro Asp Gly Arg
                245                 250                 255
Arg Thr Arg Leu Ser Val Ile Gly Phe Asp Lys Lys Met Lys Ala Arg
            260                 265                 270
Glu Ile Ala Tyr Ser Asp Ala Ile Pro Trp
            275                 280
```

<210> SEQ ID NO 47
<211> LENGTH: 3963
<212> TYPE: DNA
<213> ORGANISM: Salmon pancreas disease virus (PDV)
<300> PUBLICATION INFORMATION:
<308> DATABASE ACCESSION NUMBER: Genbank/AJ316244
<309> DATABASE ENTRY DATE: 2005-04-15
<313> RELEVANT RESIDUES IN SEQ ID NO: (7869)...(11831)

<400> SEQUENCE: 47
atgtttccca tgcaattcac caactcagcc tatcgccaga tggagcccat gtttgcaccg 60
ggttcccgag gacaagtaca gccgtaccgg ccgcgcacta agcgccgcca ggagccgcaa 120
gtcggcaacg ccgccattac tgccctcgcg aaccagatga gtgcgctcca gttgcaggta 180
gctggacttg ccggccaggc aagggtggac cgccgtgggc caagacgtgt tcagaagaac 240
aagcagaaga agaagaactc ttccaacgga gaaaaaccca aagagaagaa gaagaagcaa 300
aaacaacagg agaagaaggg aagcggtggc gaaaaagtca agaagactag gaaccgaccc 360

```
gggaaggagg taaggatctc cgtaaagtgt gcccgacaga gcaccttccc cgtgtaccac   420
gaaggtgcta tatccggcta cgctgtgctg attggatctc gcgtattcaa gccggcacac   480
gtgaagggta agatcgacca ccctgaactg gcagacatca agttccaggt cgccgaggac   540
atggacctcg aagcagctgc gtacccgaag agcatgcgag accaagcggc tgaaccagcg   600
accatgatgg acagagtgta caactgggag tatggcacta tcagagtgga ggataatgtc   660
ataatcgacg caagcggtag gggcaagccg ggtgacagtg gcagggccat caccgacaac   720
tcgggaaagg ttgttggtat tgtcctcgga ggaggacccg atggcaggcg cacacgcctc   780
tccgtgatag gtttcgacaa gaagatgaag gctagggaga tcgcctacag tgatgccata   840
ccttggacac gcgctccggc cctcctgctg ctgcctatgg ttattgtctg cacctacaat   900
tccaacacct tcgattgctc caaaccgtcc tgccaggact gctgcattac tgctgaacca   960
gagaaggcca tgaccatgct gaaggacaat ctgaacgacc cgaactactg ggacctactc  1020
attgctgtca ccacctgtgg ctccgcccgg agaaagaggg ctgtgtctac gtcgcctgcc  1080
gcctttacg acacacagat cctcgccgcc cacgcagctg cctccccata cagggcgtac  1140
tgccccgatt gtgacggaac agcgtgtatc tcgccgatag ccatcgacga ggtggtgagc  1200
agtggcagcg accacgtcct ccgcatgcgg gttggttctc aatcgggagt gaccgctaag  1260
ggtggtgcgg cgggtgaaac ctctctgcga tacctgggaa gggacgggaa ggttcacgcc  1320
gcagacaaca cgcgactcgt ggtgcgcacg actgcaaagt gcgacgtgct gcaggccact  1380
ggccactaca tcctggccaa ctgcccagtg gggcagagcc taaccgttgc ggccacactg  1440
gatggcaccc ggcatcaatg caccacggtt ttcgaacacc aagtaacgga gaagttcacc  1500
agagaacgca gcaagggcca ccatctgtcc gacatgacca gaaatgcac cagatttttcc  1560
actacaccaa aaaagtccgc cctctacctc gttgatgtgt atgacgctct gccgatttct  1620
gtagagatta gcaccgtcgt aacatgcagc gacagccagt gcacagtgag ggtgccacct  1680
ggtaccacag tgaaattcga caagaaatgc aagagcgctg actcggcaac cgtcactttc  1740
accagcgact cccagacgtt tacgtgtgag gagccagtcc taacggctgc cagtatcacc  1800
cagggcaagc cacacctcag atcggcaatg ttgcctagcg gaggcaagga agtgaaagca  1860
aggatcccgt tccgttccc gccggaaacc gcaacttgca gagtgagtgt agccccactg  1920
ccgtcgatca cctacgagga aagcgatgtc ctgctagccg gtaccgcaaa ataccctgtg  1980
ctgctaacca cacggaacct tggttttccat agcaacgcca catccgaatg gatccagggc  2040
aagtacctgc gccgcatccc ggtcacgcct caagggatcg agctaacatg gggaaacaac  2100
gcgccgatgc acttttggtc atccgtcagg tacgcatccg gggacgctga tgcgtacccc  2160
tgggaacttc tggtgtacca caccaagcac catccagagt acgcgtgggc gtttgtagga  2220
gttgcatgcg gcctgctggc tatcgcagcg tgcatgtttg cgtgcgcatg cagcagggtg  2280
cggtactctc tggtcgccaa cacgttcaac tcgaacccac caccattgac cgcactgact  2340
gcagcactgt gttgcatacc aggggctcgc gcggaccaac cctacttgga catcattgcc  2400
tacttgtgga ccaacagcaa agtggccttc gggctacaat tgcggcgcc cgtggcctgt  2460
gtgctcatca ttacatacgc ccttaggcac tgcagattgt gctgcaagtc ttttttaggg  2520
gtaagagggt ggtcagccct gctggtcatc cttgcgtatg tacagagctg caagagctac  2580
gaacacaccg tggtggtccc aatggatcca agagcccgt cgtacgaagc agtgataaac  2640
cggaatggga tgatccatt gaagctgacc atctcagtga atttcaccgt catctccacca  2700
actacggctc tggaatattg gacctgcgca ggagtcccca tcgtcgagcc gccccatgtg  2760
```

-continued

| | |
|---|---|
| ggctgctgca cgtcggtgtc ctgcccctct gacctctcta cgctgcatgc gtttactggc | 2820 |
| aaagctgtct ccgacgtgca ctgcgatgtg cacacaaacg tgtaccccct gttgtggggc | 2880 |
| gcggctcact gcttctgttc caccgagaat acacaggtca gcgctgtggc agccaccgtt | 2940 |
| tctgagttct gtgcccagga ctcagagcgt gccgaagcgt tcagcgtaca cagcagctca | 3000 |
| gtcaccgctg aggtcctggt gacgcttggt gaagtggtga cggcagtcca cgtttacgtg | 3060 |
| gacggggtaa catcagccag gggcactgac ctcaagatcg tggctggacc aataacaacc | 3120 |
| gactactccc cattcgatcg caaagtagtc cgcatcggcg aagaggtcta taactatgac | 3180 |
| tggcctcctt acggggctgg ccgaccaggc acattcggag acattcaagc taggtcaacc | 3240 |
| aactatgtca acccaacga tctgtatggg gacatcggaa ttgaagtact gcagccgact | 3300 |
| aacgaccacg tacatgtggc ttacacgtat acgacctctg ggttactgcg ttggctgcag | 3360 |
| gacgctccga aaccactcag tgtcacagca ccgcacggtt gtaagatcag tgccaatccg | 3420 |
| ctcctggccc tcgattgtgg ggttggtgcc gtccccatgt ccatcaacat tccggacgcg | 3480 |
| aagtttaccc gcaaattaaa ggatccgaaa ccatcggccc tgaaatgcgt ggtggacagc | 3540 |
| tgcgagtacg gggtggacta cggggcgcc gccacgatca cctacgaggg ccacgaggcc | 3600 |
| gggaagtgcg ggattcattc cctgacacca ggagtccccc tgagaacatc ggtggttgaa | 3660 |
| gtggttgctg cgccaatac cgtcaaaacg accttctcct cacccacgcc cgaggttgca | 3720 |
| ctcgaggtag agatctgttc ggcaatagtg aagtgcgctg gtgagtgcac tccaccgaag | 3780 |
| gaacatgtgg tcgcaaccag gcctcgccat ggcagcgacc ctggaggcta catctccggg | 3840 |
| cccgcaatgc gctgggccgg agggattgta gggaccctag tggtcctgtt ccttatcctt | 3900 |
| gccgtcatct actgcgtggt gaagaagtgc cgctccaaaa gaatccggat agtcaagagc | 3960 |
| taa | 3963 |

<210> SEQ ID NO 48
<211> LENGTH: 1320
<212> TYPE: PRT
<213> ORGANISM: Salmon pancreas disease virus (PDV)
<300> PUBLICATION INFORMATION:
<308> DATABASE ACCESSION NUMBER: Genbank/CAC87722
<309> DATABASE ENTRY DATE: 2005-04-15

<400> SEQUENCE: 48

```
Met Phe Pro Met Gln Phe Thr Asn Ser Ala Tyr Arg Gln Met Glu Pro
1               5                   10                  15

Met Phe Ala Pro Gly Ser Arg Gly Gln Val Gln Pro Tyr Arg Pro Arg
            20                  25                  30

Thr Lys Arg Arg Gln Glu Pro Gln Val Gly Asn Ala Ala Ile Thr Ala
        35                  40                  45

Leu Ala Asn Gln Met Ser Ala Leu Gln Leu Gln Val Ala Gly Leu Ala
    50                  55                  60

Gly Gln Ala Arg Val Asp Arg Arg Gly Pro Arg Arg Val Gln Lys Asn
65                  70                  75                  80

Lys Gln Lys Lys Lys Asn Ser Ser Asn Gly Glu Lys Pro Lys Glu Lys
                85                  90                  95

Lys Lys Lys Gln Lys Gln Gln Glu Lys Lys Gly Ser Gly Gly Glu Lys
            100                 105                 110

Val Lys Lys Thr Arg Asn Arg Pro Gly Lys Glu Val Arg Ile Ser Val
        115                 120                 125

Lys Cys Ala Arg Gln Ser Thr Phe Pro Val Tyr His Glu Gly Ala Ile
    130                 135                 140
```

-continued

```
Ser Gly Tyr Ala Val Leu Ile Gly Ser Arg Val Phe Lys Pro Ala His
145                 150                 155                 160

Val Lys Gly Lys Ile Asp His Pro Glu Leu Ala Asp Ile Lys Phe Gln
            165                 170                 175

Val Ala Glu Asp Met Asp Leu Glu Ala Ala Tyr Pro Lys Ser Met
        180                 185                 190

Arg Asp Gln Ala Ala Glu Pro Ala Thr Met Met Asp Arg Val Tyr Asn
            195                 200                 205

Trp Glu Tyr Gly Thr Ile Arg Val Glu Asp Asn Val Ile Ile Asp Ala
        210                 215                 220

Ser Gly Arg Gly Lys Pro Gly Asp Ser Gly Arg Ala Ile Thr Asp Asn
225                 230                 235                 240

Ser Gly Lys Val Val Gly Ile Val Leu Gly Gly Pro Asp Gly Arg
            245                 250                 255

Arg Thr Arg Leu Ser Val Ile Gly Phe Asp Lys Lys Met Lys Ala Arg
        260                 265                 270

Glu Ile Ala Tyr Ser Asp Ala Ile Pro Trp Thr Arg Ala Pro Ala Leu
        275                 280                 285

Leu Leu Leu Pro Met Val Ile Val Cys Thr Tyr Asn Ser Asn Thr Phe
        290                 295                 300

Asp Cys Ser Lys Pro Ser Cys Gln Asp Cys Cys Ile Thr Ala Glu Pro
305                 310                 315                 320

Glu Lys Ala Met Thr Met Leu Lys Asp Asn Leu Asn Asp Pro Asn Tyr
            325                 330                 335

Trp Asp Leu Leu Ile Ala Val Thr Thr Cys Gly Ser Ala Arg Arg Lys
        340                 345                 350

Arg Ala Val Ser Thr Ser Pro Ala Ala Phe Tyr Asp Thr Gln Ile Leu
        355                 360                 365

Ala Ala His Ala Ala Ala Ser Pro Tyr Arg Ala Tyr Cys Pro Asp Cys
        370                 375                 380

Asp Gly Thr Ala Cys Ile Ser Pro Ile Ala Ile Asp Glu Val Val Ser
385                 390                 395                 400

Ser Gly Ser Asp His Val Leu Arg Met Arg Val Gly Ser Gln Ser Gly
            405                 410                 415

Val Thr Ala Lys Gly Ala Ala Gly Glu Thr Ser Leu Arg Tyr Leu
        420                 425                 430

Gly Arg Asp Gly Lys Val His Ala Ala Asp Asn Thr Arg Leu Val Val
        435                 440                 445

Arg Thr Thr Ala Lys Cys Asp Val Leu Gln Ala Thr Gly His Tyr Ile
        450                 455                 460

Leu Ala Asn Cys Pro Val Gly Gln Ser Leu Thr Val Ala Ala Thr Leu
465                 470                 475                 480

Asp Gly Thr Arg His Gln Cys Thr Thr Val Phe Glu His Gln Val Thr
            485                 490                 495

Glu Lys Phe Thr Arg Glu Arg Ser Lys Gly His His Leu Ser Asp Met
        500                 505                 510

Thr Lys Lys Cys Thr Arg Phe Ser Thr Thr Pro Lys Lys Ser Ala Leu
        515                 520                 525
```

-continued

```
Tyr Leu Val Asp Val Tyr Asp Ala Leu Pro Ile Ser Val Glu Ile Ser
    530                 535                 540

Thr Val Val Thr Cys Ser Asp Ser Gln Cys Thr Val Arg Val Pro Pro
545                 550                 555                 560

Gly Thr Thr Val Lys Phe Asp Lys Lys Cys Lys Ser Ala Asp Ser Ala
                565                 570                 575

Thr Val Thr Phe Thr Ser Asp Ser Gln Thr Phe Thr Cys Glu Glu Pro
            580                 585                 590

Val Leu Thr Ala Ala Ser Ile Thr Gln Gly Lys Pro His Leu Arg Ser
        595                 600                 605

Ala Met Leu Pro Ser Gly Gly Lys Glu Val Lys Ala Arg Ile Pro Phe
    610                 615                 620

Pro Phe Pro Pro Glu Thr Ala Thr Cys Arg Val Ser Val Ala Pro Leu
625                 630                 635                 640

Pro Ser Ile Thr Tyr Glu Ser Asp Val Leu Leu Ala Gly Thr Ala
                645                 650                 655

Lys Tyr Pro Val Leu Leu Thr Thr Arg Asn Leu Gly Phe His Ser Asn
                660                 665                 670

Ala Thr Ser Glu Trp Ile Gln Gly Lys Tyr Leu Arg Arg Ile Pro Val
            675                 680                 685

Thr Pro Gln Gly Ile Glu Leu Thr Trp Gly Asn Asn Ala Pro Met His
        690                 695                 700

Phe Trp Ser Ser Val Arg Tyr Ala Ser Gly Asp Ala Asp Ala Tyr Pro
705                 710                 715                 720

Trp Glu Leu Leu Val Tyr His Thr Lys His His Pro Glu Tyr Ala Trp
                725                 730                 735

Ala Phe Val Gly Val Ala Cys Gly Leu Leu Ala Ile Ala Ala Cys Met
            740                 745                 750

Phe Ala Cys Ala Cys Ser Arg Val Arg Tyr Ser Leu Val Ala Asn Thr
        755                 760                 765

Phe Asn Ser Asn Pro Pro Leu Thr Ala Leu Thr Ala Ala Leu Cys
    770                 775                 780

Cys Ile Pro Gly Ala Arg Ala Asp Gln Pro Tyr Leu Asp Ile Ile Ala
785                 790                 795                 800

Tyr Leu Trp Thr Asn Ser Lys Val Ala Phe Gly Leu Gln Phe Ala Ala
                805                 810                 815

Pro Val Ala Cys Val Leu Ile Ile Thr Tyr Ala Leu Arg His Cys Arg
            820                 825                 830

Leu Cys Cys Lys Ser Phe Leu Gly Val Arg Gly Trp Ser Ala Leu Leu
        835                 840                 845

Val Ile Leu Ala Tyr Val Gln Ser Cys Lys Ser Tyr Glu His Thr Val
    850                 855                 860

Val Val Pro Met Asp Pro Arg Ala Pro Ser Tyr Glu Ala Val Ile Asn
865                 870                 875                 880

Arg Asn Gly Tyr Asp Pro Leu Lys Leu Thr Ile Ser Val Asn Phe Thr
                885                 890                 895

Val Ile Ser Pro Thr Thr Ala Leu Glu Tyr Trp Thr Cys Ala Gly Val
            900                 905                 910

Pro Ile Val Glu Pro Pro His Val Gly Cys Cys Thr Ser Val Ser Cys
        915                 920                 925

Pro Ser Asp Leu Ser Thr Leu His Ala Phe Thr Gly Lys Ala Val Ser
    930                 935                 940

Asp Val His Cys Asp Val His Thr Asn Val Tyr Pro Leu Leu Trp Gly
945                 950                 955                 960
```

```
Ala Ala His Cys Phe Cys Ser Thr Glu Asn Thr Gln Val Ser Ala Val
                965                 970                 975

Ala Ala Thr Val Ser Glu Phe Cys Ala Gln Asp Ser Glu Arg Ala Glu
            980                 985                 990

Ala Phe Ser Val His Ser Ser Val Thr Ala Glu Val Leu Val Thr
        995                1000                1005

Leu Gly Glu Val Val Thr Ala Val His Val Tyr Val Asp Gly Val Thr
   1010                1015                1020

Ser Ala Arg Gly Thr Asp Leu Lys Ile Val Ala Gly Pro Ile Thr Thr
1025                1030                1035                1040

Asp Tyr Ser Pro Phe Asp Arg Lys Val Val Arg Ile Gly Glu Val
            1045                1050                1055

Tyr Asn Tyr Asp Trp Pro Pro Tyr Gly Ala Gly Arg Pro Gly Thr Phe
        1060                1065                1070

Gly Asp Ile Gln Ala Arg Ser Thr Asn Tyr Val Lys Pro Asn Asp Leu
    1075                1080                1085

Tyr Gly Asp Ile Gly Ile Glu Val Leu Gln Pro Thr Asn Asp His Val
    1090                1095                1100

His Val Ala Tyr Thr Tyr Thr Thr Ser Gly Leu Leu Arg Trp Leu Gln
1105                1110                1115                1120

Asp Ala Pro Lys Pro Leu Ser Val Thr Ala Pro His Gly Cys Lys Ile
            1125                1130                1135

Ser Ala Asn Pro Leu Leu Ala Leu Asp Cys Gly Val Gly Ala Val Pro
            1140                1145                1150

Met Ser Ile Asn Ile Pro Asp Ala Lys Phe Thr Arg Lys Leu Lys Asp
        1155                1160                1165

Pro Lys Pro Ser Ala Leu Lys Cys Val Val Asp Ser Cys Glu Tyr Gly
        1170                1175                1180

Val Asp Tyr Gly Gly Ala Ala Thr Ile Thr Tyr Glu Gly His Glu Ala
1185                1190                1195                1200

Gly Lys Cys Gly Ile His Ser Leu Thr Pro Gly Val Pro Leu Arg Thr
            1205                1210                1215

Ser Val Val Glu Val Val Ala Gly Ala Asn Thr Val Lys Thr Thr Phe
            1220                1225                1230

Ser Ser Pro Thr Pro Glu Val Ala Leu Glu Val Glu Ile Cys Ser Ala
        1235                1240                1245

Ile Val Lys Cys Ala Gly Glu Cys Thr Pro Pro Lys Glu His Val Val
        1250                1255                1260

Ala Thr Arg Pro Arg His Gly Ser Asp Pro Gly Gly Tyr Ile Ser Gly
1265                1270                1275                1280

Pro Ala Met Arg Trp Ala Gly Gly Ile Val Gly Thr Leu Val Val Leu
            1285                1290                1295

Phe Leu Ile Leu Ala Val Ile Tyr Cys Val Val Lys Lys Cys Arg Ser
        1300                1305                1310

Lys Arg Ile Arg Ile Val Lys Ser
        1315                1320
```